US011091433B2

(12) United States Patent
Wall et al.

(10) Patent No.: US 11,091,433 B2
(45) Date of Patent: *Aug. 17, 2021

(54) METHOD FOR PREPARATION OF N-ACETYL CYSTEINE AMIDE AND DERIVATIVES THEREOF

(71) Applicant: NACUITY PHARMACEUTICALS, INC., Fort Worth, TX (US)

(72) Inventors: G. Michael Wall, Fort Worth, TX (US); Doug Johnson, Arvada, CO (US); Anja Rubenstein, Florence, SC (US); Rodney Tucker, Hartsville, SC (US); Josh Bolger, Florence, SC (US)

(73) Assignee: Nacuity Pharmaceutials, Inc., Fort Worth, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/818,416

(22) Filed: Mar. 13, 2020

(65) Prior Publication Data

US 2020/0277258 A1 Sep. 3, 2020

Related U.S. Application Data

(63) Continuation-in-part of application No. 16/137,262, filed on Sep. 20, 2018, now Pat. No. 10,590,073.
(Continued)

(51) Int. Cl.
*C07C 319/26* (2006.01)
*C07C 319/22* (2006.01)
(Continued)

(52) U.S. Cl.
CPC .......... *C07C 319/26* (2013.01); *C07C 319/06* (2013.01); *C07C 319/22* (2013.01);
(Continued)

(58) Field of Classification Search
None
See application file for complete search history.

(56) References Cited

U.S. PATENT DOCUMENTS 3,340,147 A 9/1967 Martin et al.
6,420,429 B1 7/2002 Atlas et al.
(Continued)

FOREIGN PATENT DOCUMENTS

EP 1975621 A1 1/2008
GB 1114369 A 5/1968
(Continued)

OTHER PUBLICATIONS

Haywood ("Liquid Dosage Forms Extemporaneously Prepared from Commercially Available Products-Considering New Evidence on Stability" J. Pharm Pham Sci 16(3), 2013, p. 441-445) (Year: 2013).*

(Continued)

*Primary Examiner* — Amy C Bonaparte
(74) *Attorney, Agent, or Firm* — Edwin S. Flores; Chalker Flores, LLP

(57) ABSTRACT

The present invention includes methods for making and isolating N-acetylcysteine amide, (2R,2R')-3,3'-disulfanediyl bis(2-acetamidopropanamide, diNACA), intermediates and derivatives thereof comprising: contacting cystine with an alcohol and a chlorinating reagent to form an organic solution containing L-cystine dimethylester dihydrochloride; combining dried or undried L-cystine dimethylester dihydrochloride with a triethylamine, an acetic anhydride, and an acetonitrile to form a di-N-acetylcystine dimethylester; mixing dried di-N-acetylcystine dimethylester with ammonium hydroxide to form a di-N-acetylcystine amide
(Continued)

(diNACA); and separating dried di-N-acetylcystine dimethylester into N-acetylcysteine amide with dithiothreitol, triethylamine and an alcohol.

29 Claims, 16 Drawing Sheets

Related U.S. Application Data

(60) Provisional application No. 62/561,129, filed on Sep. 20, 2017.

(51) Int. Cl.
  C07C 323/25 (2006.01)
  C07C 319/06 (2006.01)
  C07C 319/28 (2006.01)
  C07C 323/41 (2006.01)
  C07C 323/58 (2006.01)
  C07C 323/59 (2006.01)

(52) U.S. Cl.
  CPC .......... *C07C 319/28* (2013.01); *C07C 323/25* (2013.01); *C07C 323/41* (2013.01); *C07C 323/58* (2013.01); *C07C 323/59* (2013.01)

(56) References Cited

U.S. PATENT DOCUMENTS

| | | | |
|---|---|---|---|
| 9,763,902 | B2 | 9/2017 | Warner et al. |
| 9,889,103 | B2 | 2/2018 | Warner et al. |
| 10,590,073 | B2* | 3/2020 | Wall ...................... C07C 319/06 |
| 2005/0112572 | A1 | 5/2005 | Pincemail et al. |
| 2009/0234011 | A1 | 9/2009 | Goldstein |
| 2012/0150029 | A1 | 6/2012 | Debuc |
| 2013/0303436 | A1 | 11/2013 | Wilson |
| 2017/0333375 | A1 | 11/2017 | Campochiaro et al. |
| 2017/0370945 | A1 | 12/2017 | Campochiaro et al. |
| 2019/0135741 | A1* | 5/2019 | Wall ...................... A61K 9/0048 |
| 2020/0217852 | A1* | 7/2020 | Wall .................. G01N 33/6815 |
| 2020/0222344 | A1* | 7/2020 | Wall ...................... A61K 31/16 |

FOREIGN PATENT DOCUMENTS

| | | |
|---|---|---|
| WO | 2003016527 A2 | 2/2003 |
| WO | 2004012652 A2 | 2/2004 |
| WO | 2006/116353 A2 | 11/2006 |
| WO | 2013263545 A1 | 10/2013 |
| WO | 2014100361 A1 | 6/2014 |
| WO | 2015148880 A1 | 10/2015 |
| WO | 2016073829 A2 | 5/2016 |
| WO | 2016073931 A1 | 5/2016 |
| WO | 2017161318 A1 | 9/2017 |
| WO | 2019/060623 A1 | 3/2019 |
| WO | 2019/094383 A1 | 5/2019 |

OTHER PUBLICATIONS

SciFinder entry for the compound having CAS registry No. 16359-16-3, downloaded on Aug. 14, 2020 (Year: 2020).*
Riley, et al., "Glutathione in the aqueous humor of human and other species." Investigative ophthalmology & visual science, (1980), 9(1):94-96.
Schimel, et al., "N-Acetylcysteine Amide (NACA) Prevents Retinal Degeneration by Up-Regulating Reduced Glutathione Production and Reversing Lipid Peroxidation." The American Journal of Pathology, (2011), 178 (5):2032-2043.
Shen, et al., "Oxidative damage is a potential cause of cone cell death in retinitis pigmentosa." J Cell Physiol, (2005), 203(3):457-64.
Shen, et al., "Oxidative damage in age-related macular degeneration," Histology and Histopathology (2007), 22 (12):1301-1308.
Shintani, et al., "Review and Update: Current treatment trends for Patients with Retinitis Pigmentosa," Optometry (2009), 80:384-401.
Supelco "Methanolic H2SO4 (10°/o v/v)" 1997, Sigma-Aldrich Co., 2 Pages.
Tse, et al., "High-dose N-acetylcysteinine in stable COPD: the 1-year, double-blind, randomized, placebo-controlled HIACE study." Chest, (2013). 144(1):106-118.
Tuson, et al., "Overexpression of CERKL, a gene responsible for retinitis pigmentosa in humans, protects cells from apoptosis induced by oxidative stress." Mol Vis. (2009), 15:168-80.
Usui, et al., "Overexpression of SOD in retina: Need for increase in H2O2-detoxifying enzyme in same cellular compartment," Free Radical Biology and Medicine (2011), 51(7):1347-1354.
Usui et al., "Increased expression of catalase and superoxide dismutase 2 reduces cone cell death in retinitis pigmentosa." Mol Ther J Am Soc Gene Ther. (2009), 17(5):778-86.
Usui, et al., "NADPH oxidase plays a central role in cone cell death in retinitis pigmentosa." J Neurochem. (2009), 110 (3):1028-37.
Wu, et al., "Effects of N-acetylcysteine amide (NACA, a thiol antioxidant on radiation-induced cytotoxicity in Chenese hamster ovary cells," Life Sciences (2008), 82:1122-1130.
Yu, et al., "Intraretinal oxygen levels before and after photoreceptor loss in the RCS rat." Invest Ophthalmol Vis Sci, (2000), 41(12):3999-4006.
Betteridge, What is Oxidative Stress? Metabolism, vol. 49, No. 2, Feb. 2000, pp. 3-8.
K. Boone, "The K-Zone: Biophysical Data Tables", 1994-2006.
Maeda et al., "Important Role of the 3-Mercaptopropionamide . . . ", JOC Article, 2005. 70. 8338-8343.
Niemeyer, "Selective Rod-and Cone-ERG Responses in Retinal Degenerations", Digital Journal of Ophthalmology, 1998, vol. 4, No. 10, 1998.
Sekhon, "Exploiting the Power of Stereochemistry in Drugs . . . ", Journal of Modern Medicinal Chemistry, 2013, 10-36.
Minozzi, M., et al., "An Insight into the Radical Thiol/Yne Coupling: The Emergence of Arylalkyne-Tagged Sugars for the Direct Photoinduced Glycosylation of Cysteine-Containing Peptides", J. Org. Chem., 2011, 76, 450-459.
Tobwala et al. "N-acetylcysteine Amide (NACA), a Novel GSH Prodrug: Its Metabolism and Implications in Health", Labrou, 2013, Capter VI. ISBN:978-1-62417-460-5.
Ates, et al., "Antioxidant and free radical scavenging properties of N-acetylcysteine amide (NACA) and comparison with N-acetylcysteine (NAC)." Free Radic Res. (2008), 42(4):372-7.
Bean, et al., "Comparative evaluation of antioxidant reactivity within obstructed and control rabbit urinary bladder tissue using FRAP and CUPRAC assays," Molecular and Cellular Biochemistry (2008) 323(1-2):139-142.
Bernardes, et al., "From Disulfide- to Thioether-Linked Glycoproteins" Angewandte Chemie, Supporting Information (2008), S1-S97.
Buss, et al., "Protein carbonyl measurement by a sensitive ELISA method." Free Radic Biol Med, (1997), 23(3):361-6.
Campochiaro, et al. "Is there Excess Oxidative Stress and Damage in Eyes of Patients with Retinitis Pigmentosa?" Antioxidants & Redox Signaling, (2015) 23(7):643-648.
Campochiaro, et al. "The Mechanism of Cone Cell Death in Retinitis Pigmentosa", Progress in Retinal and Eye Research (2018), 62:24-37.
Chastain, et al. "Distribution of topical ocular nepafenac and its active metabolite amfenac to the posterior segment of the eye." Exp Eye Res (2016), 145:58-67.
Davies, et al., "Measurements of protein carbonyls, ortho- and meta-tyrosine and oxidative phosphorylation complex activity in mitochondria from young and old rats." Free Radic Biol Med, (2001), 31(2):181-90.
Devries, et al. "N-acetyH-cysteine." J Cell Biochem Suppl (1993), 17F:270-277.
Dietz, et al., "Photochemical Reduction of 5-Bromouracil by Cysteine Derivatives and Coupling of 5-Bromouracil to cystine Derivatives," Photochemistry and Photobiology (1989), 49(2):121-129.
Dong, et al., "Compared with N-acetylcysteine (NAC), N-Acetylcysteinne Amid (NACA) Provides Increased Protein of

(56) References Cited

OTHER PUBLICATIONS

Cone Function in a Model of Retinitis Pigmentosa." Investigative Ophthalmology & Visual Science, (2014), 55:1-2. (Abstract).
Extended European Search Report for EP 15770142.6 dated Oct. 20, 2017.
Extended European Search Report for EP 15857309.7 dated May 23, 2018.
Extended European Search Report for EP 15858590.1 dated May 2, 2018.
Heymann, et al, "Preparation and some biological properties of the asparagine analog L-2-amino-2-carboxyethanesulfonamide" Journal of the American Chemical Society, (1959), 81:5125-5128.
International Search Report and Written Opinion PCT/US2015/059589 dated Feb. 2, 2016, 10 pg.
International Search Report and Written Opinion PCT/US2015/060172 dated Apr. 13, 2016, 12 pg.
International Search Report and Written Opinion PCT/US2018/052065 dated Jan. 10, 2019, 10 pg.
International Search Report and Written Opinion PCT/US2018/061357 dated Dec. 18, 2018, 11 pg.
International Search Report and Written Opinion PCT/US2018/059446 dated Dec. 31, 2018, 15 pg.
Jones, "Extracellular Redox State: Refining the Definition of Oxidative Stress in Aging," Rejuvenation Research (2006), 9(2):169-181.
Kahns, et al., "Prodrugs as drug delivery systems. 107. Synthesis and chemical and enzymatic hydrolysis kinetics of various mono- and diester prodrug of N-acetylcysteine." Int J Pharm (1990), 62:193-205.
Kelly, "Clinical applications of N-acetylcysteine." Altern Med Rev J Clin Ther. (1998), 3(2):114-27.
Komeima, et al., "Antioxidants reduce cone cell death in a model of retinitis pigmentosa." PNAS, (2006), 103(30):11300-11305.
Komeina, et al., "Antioxidants slow photoreceptor cell death in mouse models of retinitis pigmentosa." J Cell Physiol. (2007), 213(3):809-15.
Komeina, et al., "Blockade of neuronal nitric oxide synthase reduces cone cell death in a model of retinitis pigmentosa." Free Radic Biol Med, (2008), 45(6):905-12.
Li, et al, "A Convenient Synthesis of Amino Acid Methyl Esters", Molecules (2008), 13:1111-1119.
Lu, et al., "Effects of Different Types of Oxidative Stress in RPE Cells," J Cell Phys (2006), 206(1):119-125.
Martin, et al, "Amides of N-Acylcysteines as Mucolytic Agents", Journal of Medicinal Chemistry (1967), 10:1172-1176.
Martinez-Fernandez De La Camara, et al., Altered Antioxidant-Oxidant Status in Aqueous Humor and Peripheral Blood of Patents with Retinitis Pigmentosa, Plos One (2013), 8(9):E74223.
Park et al.: "Targeted and Reversible Blood-Retinal Barrier Disruption via Focused Ultrasound and Microbubbles" PLoS ONE (2012), 7(8):e42754.

\* cited by examiner

FIG. 4
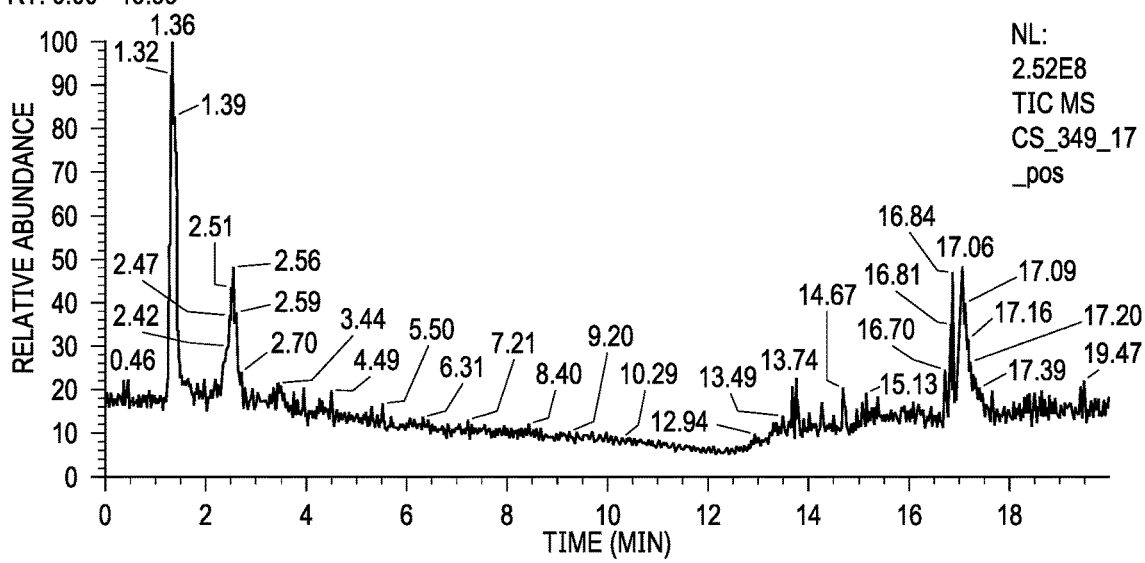
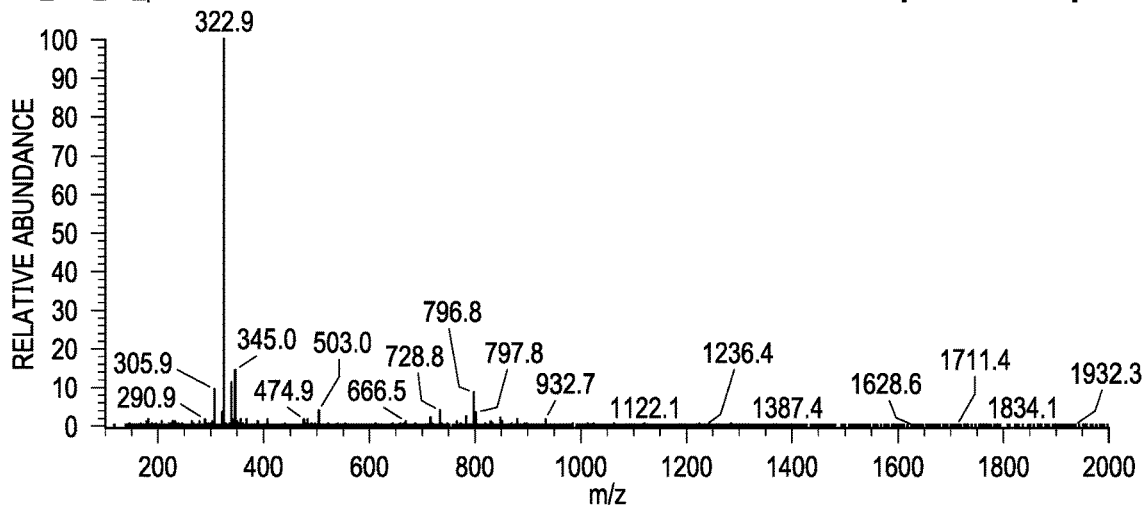
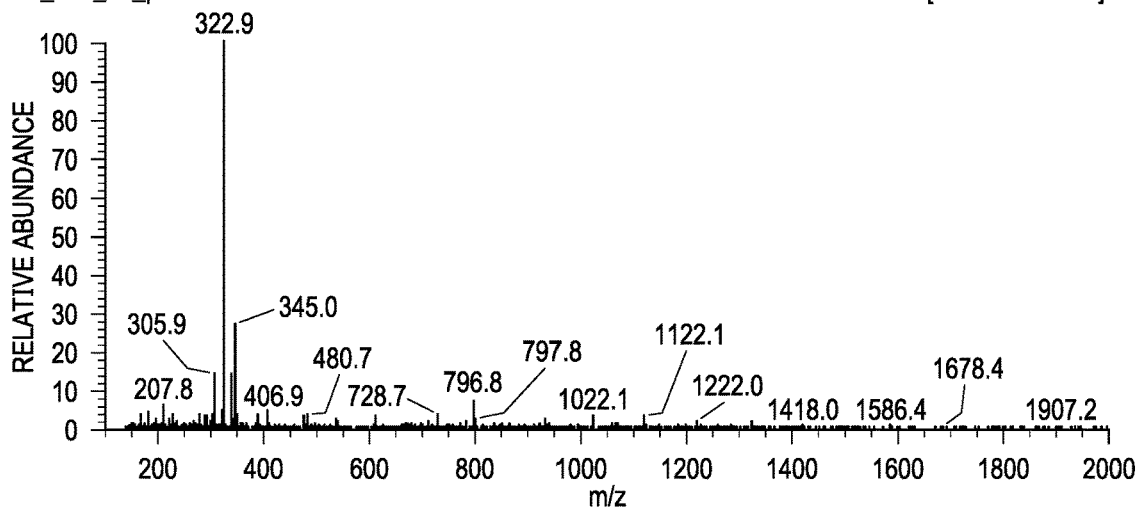

¹H NMR

| CHEMICAL SHIFT (PPM) | NUMBER PROTONS | MULTIPLICITY | COUPLING CONSTANTS | ASSIGNMENT |
|---|---|---|---|---|
| 1.88 | 3 | S | | 1 |
| 2.24 | 1 | T | J = 8.65 Hz | 2 |
| 2.64 | 1 | M | | 3 OR 4 |
| 2.78 | 1 | M | | 3 OR 4 |
| 4.30 | 1 | M | | 5 |
| 7.13 | 1 | S | | 6 OR 7 |
| 7.41 | 1 | S | | 6 OR 7 |
| 7.99 | 1 | D | J = 8.15 Hz | 8 |

HMBC AND HSQC
CORRELATIONS OBSERVED IN HSQC AND HMBC THAT HELPED
IN CONFIRMATION OF THE STRUCTURE ARE DETAILED BELOW

| ASSIGNMENT | HSQC CORRELATIONS | HMBC CORRELATIONS |
|---|---|---|
| 1 | A | D |
| 3 AND 4 | B | C AND E |
| 5 | C | B, D AND E |
| 6 | | C AND E |
| 7 | | E |
| 8 | | C AND D |

METHOD FOR PREPARATION OF N-ACETYL CYSTEINE AMIDE AND DERIVATIVES THEREOF

CROSS-REFERENCE TO RELATED APPLICATIONS

This application claims priority to U.S. Provisional Application Ser. No. 62/561,129, filed Sep. 20, 2017, entitled "Method for Preparation of N-Acetyl Cysteine Amide and Derivatives" and is a Continuation-in-Part of U.S. Ser. No. 16/137,262, filed Sep. 20, 2018, entitled "Method for Preparation of N-Acetyl Cysteine Amide and Derivatives" and has been allowed as of Mar. 17, 2020 as U.S. patent Ser. No. 10/590,073, the entire contents of which are incorporated herein by reference.

STATEMENT OF FEDERALLY FUNDED RESEARCH

None.

TECHNICAL FIELD OF THE INVENTION

The present invention relates in general to the field of methods for preparing N-Acetyl Cysteine Amide (N-acetylcysteine amide, NACA), (2R,2R')-3,3'-disulfanediyl bis(2-acetamidopropanamide, diNACA), and derivatives thereof.

BACKGROUND OF THE INVENTION

Without limiting the scope of the invention, its background is described in connection with synthesis of N-Acetyl Cysteine Amide and diNACA.

One such method is taught in U.S. Patent Publication No. 20170183302, filed by Warner, et al., entitled "Method for Preparation of N-Acetyl Cysteine Amide". Briefly, these inventors teach a process for the preparation of N-acetyl-L-cysteine amide (NACA) starting with N-acetyl-L-cysteine that involves contacting N-acetyl-L-cysteine with an organic alcohol and an inorganic acid to form an organic solution containing N-acetyl-L-cysteine ester; neutralizing the acid in the organic solution with an aqueous solution containing a base to form a neutralized mixture; separating an organic solution containing N-acetyl-L-cysteine ester from the neutralized mixture; removing the N-acetyl-L-cysteine ester from the organic solution under reduced pressure; and contacting the N-acetyl-L-cysteine ester with ammonia.

Another such method for the preparation of N-acetyl cysteine amide (NACA) was previously described by Martin, et al., entitled "Amides of N-Acylcysteines as Mucolytic Agents", J. Med. Chem. 1967, 10, 1172-1176.

However, a need remains for developing an efficient method for the effective, large-scale synthesis of N-acetyl cysteine amide that provides the product in high chemical yields and, in particular, high chemical and enantiomeric purity, without the need for chromatography.

SUMMARY OF THE INVENTION

This disclosure describes an efficient method or process for the preparation of NACA and diNACA in high chemical yields and high enantiomeric purity. Dimethyl 3,3'-disulfanediyl(2R,2'R)-bis(2-aminopropanoate) dihydrochloride is commonly referred to herein as L-cystine dimethyl ester dihydrochloride. Dimethyl 3,3'-disulfanediyl(2R,2'R)-bis(2-acetamidopropanoate) is commonly referred to herein as di-N-acetylcystine dimethyl ester or Di-NACMe. (2R,2'R)-3,3'-disulfanediylbis(2-acetamidopropanamide) is commonly referred to herein as diNACA. (R)-2-acetamido-3-mercaptopropanamide is commonly referred to herein as NACA or NPI-001 or N-acetylcysteine amide. Specifically, disclosed herein is a process comprising: contacting cystine with an alcohol and a chlorinating reagent to form an organic solution containing L-cystine dimethylester dihydrochloride; combining dried or undried L-cystine dimethylester dihydrochloride with a triethylamine, an acetic anhydride, and an acetonitrile to form a di-N-acetylcystine dimethylester; mixing dried di-N-acetylcystine dimethylester with ammonium hydroxide to form a di-N-acetylcystine amide; and reducing dried di-N-acetylcystine dimethylester into N-acetylcysteine amide with dithiothreitol, triethylamine and an alcohol. In one aspect, the alcohol is an organic alcohol selected from an alkyl alcohol, methanol, ethanol, propanol, iso-propanol or butanol. In another aspect, the step of contacting L-cystine with an alcohol and a chlorinating reagent to form an organic solution containing L-cystine dimethylester dihydrochloride is conducted at −10 to 10° C. and then heated to reflux at 65 to 70° C. to completion. In another aspect, the chlorinating agent is thionyl chloride. In another aspect, there is a solvent exchange between the contacting and the combining steps. In another aspect, the step of combining is performed at −10 to 10° C. In another aspect, a precipitate formed in the combining step that is filtered and washed with ethyl acetate before drying under vacuum. In another aspect, the step of combining uses at least 15 volumes acetonitrile at −10 to 10° C. before adding at least 4 equivalents of triethylamine followed by at least 2 equivalents of acetic anhydride. In another aspect, the organic solvent is ethyl acetate. In another aspect, the process further comprises drying the organic solution removed from the neutralized mixture with a drying agent. In another aspect, the process further comprises the step of free-basing the triethylamine from the di-N-acetylcystine dimethylester with saturated sodium bicarbonate after reaction completion. In another aspect, the ammonia is provided in the form of aqueous ammonium hydroxide. In another aspect, the contacting of the N-acetyl-L-cystine ester with ammonia is performed at 0° C. In another aspect, no metals are used in the reduction of di-N-acetylcystine dimethylester into N-acetylcysteine amide. In another aspect, the step of removing the organics under reduced pressure is performed at about 45° C. or less. In another aspect, the step of removing the organics under reduced pressure is performed at about 35° C. or less. In another aspect, the step of removing the organics under reduced pressure is performed at about 30° C. or less. In another aspect, the step of removing the organics under reduced pressure is performed at about 45° C. In another aspect, the organic solution removed from the neutralized mixture is filtered to remove solids. In another aspect, the one or more reducing agents is selected from triphenylphosphine, thioglycolic acid or dithiothreitol and the organic solvent is tetrahydrofuran (THF), dichloromethane (DCM), isopropanol (2-propanol), or ethanol.

In another embodiment, the present invention includes a compound having a formula:

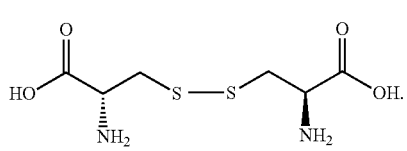

In another embodiment, the present invention includes a compound having a formula:

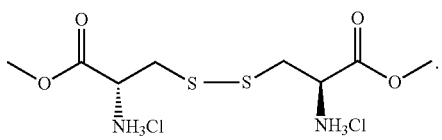

In another embodiment, the present invention includes a compound having a formula:

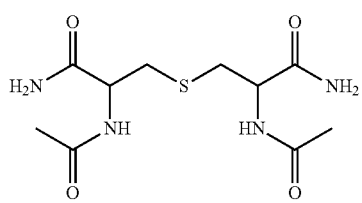 [SMILES: CC(=O)NC(CSCC(NC(C)=O)C(N)=O)C(N)=O]

In yet another embodiment, the present invention includes a process for making N-acetylcysteine amide comprising:

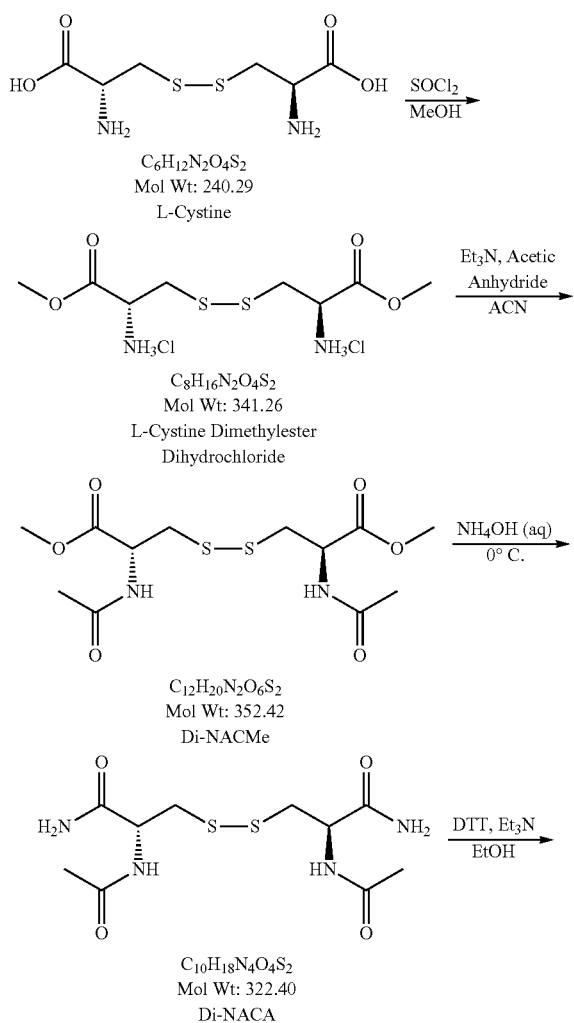

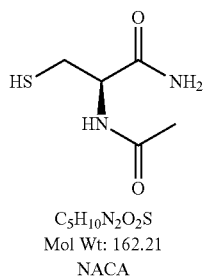

$C_5H_{10}N_2O_2S$
Mol Wt: 162.21
NACA

In another embodiment, the present invention includes a process for making N-acetylcysteine amide comprising: contacting L-cystine with an alcohol and a chlorinating reagent to form an organic solution containing L-cystine dimethylester dihydrochloride; combining dried L-cystine dimethylester dihydrochloride with a triethylamine, an acetic anhydride, and an acetonitrile to form a di-N-acetylcystine dimethylester; mixing dried di-N-acetylcystine dimethylester with ammonium hydroxide to form a di-N-acetylcystine amide; and reducing dried di-N-acetylcystine amide into N-acetylcysteine amide with dithiothreitol, triethylamine, and an alcohol, wherein the reduction is without the presence of a metal. In one aspect, the one or more reducing agents is selected from tris (2-carboxyethyl)phosphine, thioglycolic acid, dithiothreitol, and the organic solvent is THF or dichloromethane (DCM), isopropanol, or ethanol, and the base is triethylamine and or sodium bicarbonate.

In another embodiment, the present invention includes a process for making (2R,2R')-3,3'-disulfanediyl bis(2-acetamidopropanamide) (DiNACA) comprising: contacting cystine with an alcohol and a chlorinating reagent to form an organic solution containing L-cystine dimethylester dihydrochloride; combining dried or undried L-cystine dimethylester dihydrochloride with a triethylamine, an acetic anhydride, and an acetonitrile to form a di-N-acetylcystine dimethylester; and mixing dried di-N-acetylcystine dimethylester with ammonium hydroxide to form a di-N-acetylcystine amide.

BRIEF DESCRIPTION OF THE DRAWINGS

For a more complete understanding of the features and advantages of the present invention, reference is now made to the detailed description of the invention along with the accompanying figures and in which:

FIG. 4 shows results of liquid chromatography with mass spectrometric detection.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

The present invention is directed to novel methods for making N-Acetyl Cysteine Amide (NACA), and novel intermediates thereof. More particularly, the present invention takes advantage of the novel intermediates to significantly, and surprisingly, increase the efficiency of preparing NACA in both a high chemical yield and a high enantiomeric purity. Below is the basic chemical structure of NACA.

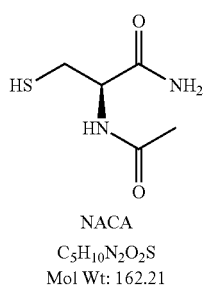

NACA
$C_5H_{10}N_2O_2S$
Mol Wt: 162.21

The following procedures may be employed for the preparation of the compound of the present invention. The starting materials and reagents used in preparing these compounds are either available from commercial suppliers such as the Aldrich Chemical Company (Milwaukee, Wis.), Bachem (Torrance, Calif.), Sigma (St. Louis, Mo.), or are prepared by methods well known to a person of ordinary skill in the art, following procedures described in such references as Fieser and Fieser's Reagents for Organic Synthesis, vols. 1-17, John Wiley and Sons, New York, N.Y., 1991; Rodd's Chemistry of Carbon Compounds, vols. 1-5 and supplements, Elsevier Science Publishers, 1989; Organic Reactions, vols. 1-40, John Wiley and Sons, New York, N.Y., 1991; March J.: Advanced Organic Chemistry, 4th ed., John Wiley and Sons, New York, N.Y.; and Larock: Comprehensive Organic Transformations, VCH Publishers, New York, 1989, relevant portions of which are incorporated herein by reference.

Figure 1:
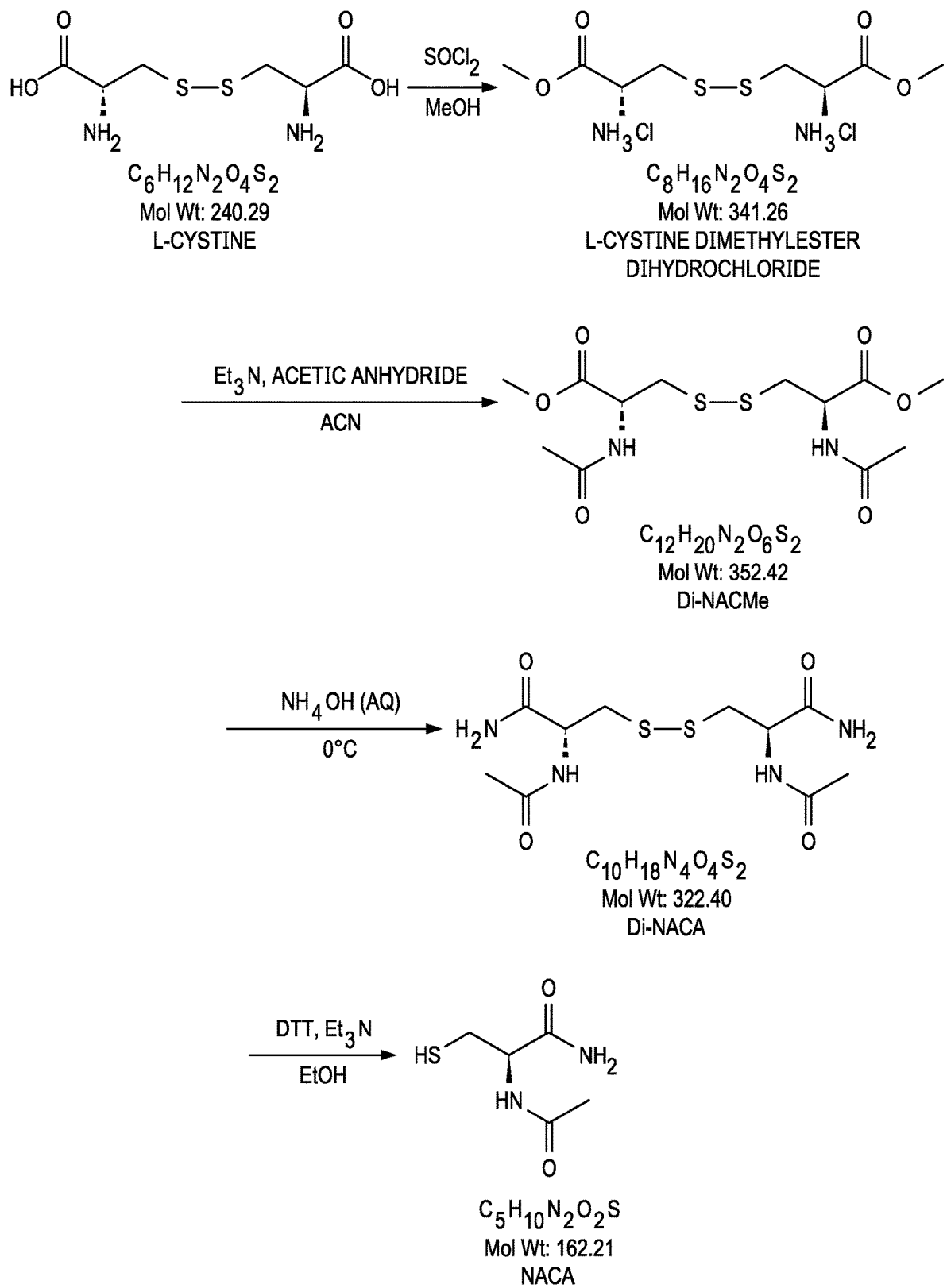
FIG. 1 shows a basic chemical synthesis of the present invention.

NACA is manufactured in 4 steps as shown in FIG. 1. The starting material is the naturally occurring L-cystine with the L conformation on both cysteine subunits. In the first step the two acid groups are protected by forming the di-methyl ester of L-cystine as the dihydrochloride salt. Alternatively, the synthesis may begin with commercially acquired L-cystine dimethyl ester dihydrochloride. In the second step the two nitrogens on the L-cystine are reacted with acetic anhydride to give diNACME which is in essence L-cystine with both acids protected as methyl esters and both primary amine groups protected with acetyl groups. Step 3 converts the methyl ester groups to primary amides. Step 4 reductively cleaves the diNACA intermediate to give NACA.

Figure 2A:
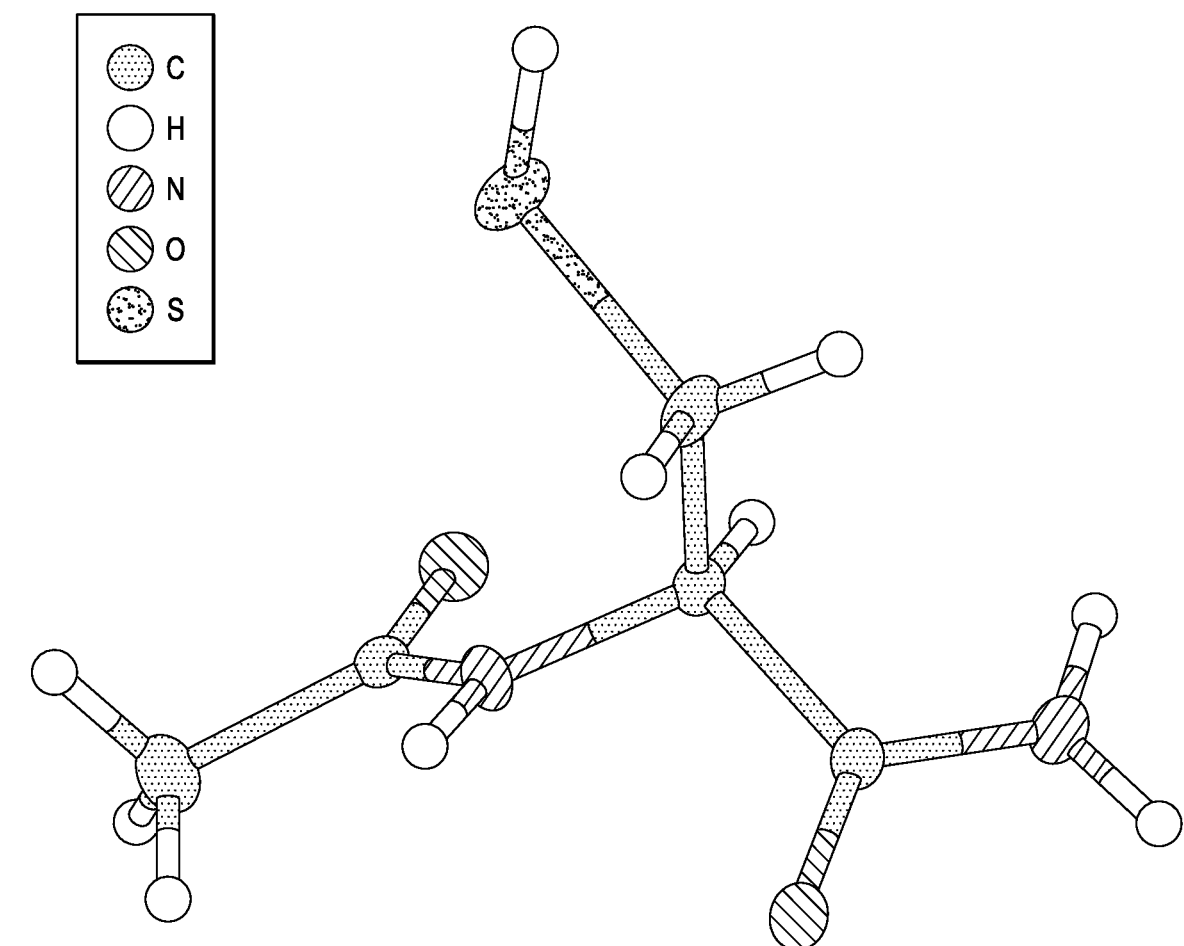
FIG. 2A shows a view of NPI-001 (NACA) molecule 'A' without atom labelling. All non-hydrogen atoms are shown with thermal ellipsoids set at the 50% probability level. Color code: Carbon, grey; H, white; O, red; S, yellow.
Figure 2B:
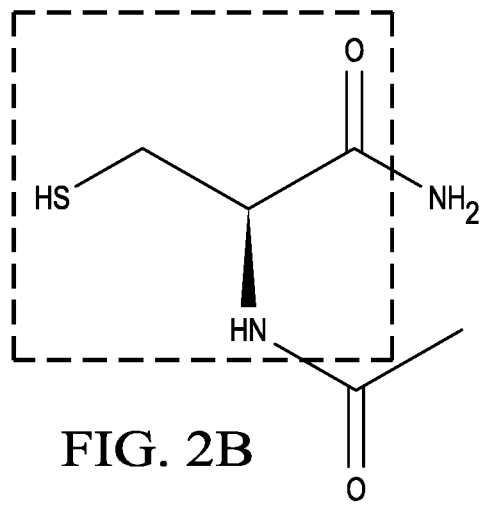
FIG. 2B shows a portion of NACA derived from starting material L-Cystine.

The preparation of NACA has one starting material that contributes significantly to the backbone of the final structure: L-cystine. In FIG. 2B, the portion of NACA that is in the dotted box is derived from L-cystine. L-Cystine provides the chiral center and the amino acid core. Two common reagents, acetic anhydride and ammonium hydroxide, provide atoms by derivatizing the carboxylic acid and primary amine, respectively.

TABLE 1

| List of Starting Materials | | |
| --- | --- | --- |
| Starting Material | Quality | Other |
| L-cystine | ≥98.5% pure | BSE/TSE-certification |

Control of Starting Materials. The quality of L-cystine may be controlled based on the specification provided by the manufacturer and/or incoming testing performed by the Contract Manufacturing Organization (CMO) as shown in Table 2.

TABLE 2

| L-Cystine Testing | | |
| --- | --- | --- |
| Attribute | Test Method | Specification/Limit |
| Appearance | Visual inspection | White powder |
| ID | NMR (USP<761>; D2O) | Conforms to structure |
| Purity[1] | Titration | 98.5-101.0% |
| Optical Rotation | Vendor method | −215 to −225° |

[1]A use test may be substituted for the purity test

Reagents and Solvents. A list of reagents and solvents used in each step of the manufacturing process is provided in Table 3 and Table 4, respectively.

TABLE 3

List of Reagents

| Step | Reagent | Quality |
|---|---|---|
| 1 | Thionyl chloride | ≥97% |
| 2, 4 | Triethylamine | ≥99% |
| 2 | Acetic anhydride | ≥99% |
| 2 | Sodium bicarbonate | ≥99% |
| 2 | Sodium sulfate (anhydrous) | — |
| 3 | Ammonium Hydroxide | 28-32% |
| 4 | Dithiothreitol | ≥98% |

TABLE 4

List of Solvents

| Step | Solvent | Quality |
|---|---|---|
| 1 | Methanol | ≥99% |
| 1, 4 | methyl t-Butyl Ether (MTBE) | ≥99% |
| 2 | Acetonitrile | ≥99% |
| 2 | Ethyl acetate | ≥99% |
| 3, 4 | EtOH | 89.0-92.0% |

In the first step, the dimethyl ester of L-cystine was formed. L-cystine and methanol were cooled to −10° C. before slowly adding thionyl chloride. The skilled artisan will recognize methanol can be substituted with other similar reactive alcohols, and/or other alternative carboxylic acid activating agents (e.g., oxalyl chloride, CDI, etc). The slurry was then heated to reflux to produce a solution. Initially, the reaction was held for 4 hours before proceeding to the workup. Using HPLC it was found to not achieve full conversion. Holding the reaction at reflux for 16 hours proved to be effective for conversion. Upon verifying reaction completion, the solution was solvent-exchanged into ethyl ether. Depending on the method of making, other such solvent may also be used, e.g., methyl tert-butyl ether (MTBE). MTBE has proven to be an effective replacement for ethyl ether, as such the solution can be solvent-exchanged successfully into MTBE, and can also be used for washes. The white solids were filtered and washed with MTBE before drying at 45° C. under vacuum to a yield of 95-99% with a purity of 96-99%.

In Step 2, the L-cystine dimethylester dichydrochloride is converted to di-N-acetylcystine dimethylester, DiNACME. L-cystine dimethylester dihydrochloride, as a slurry in acetonitrile, is cooled to 0±5° C. To the cooled solution is first added at least 4 equivalents of triethylamine followed by at least 2 equivalents of acetic anhydride while maintaining an internal temperature of ≤5° C. throughout the additions. After aging for not less than 30 minutes, reaction completion is confirmed by HPLC. To the reaction mixture is added ethyl acetate and an aqueous workup is performed. Upon completion of the aqueous workup, the organic solution is fully exchanged into ethyl acetate by vacuum distillation of the acetonitrile and replacement with ethyl acetate, several times. The product, di-N-acetylcystine dimethylester, is isolated by filtration and dried to a 73-75% yield with a purity of 93-97%. Step 2 can be accomplished in a couple of different ways. While not as efficient, the L-cystine dimethylester dihydrochloride was free-based using 300 weigh percent amberlyst-A21 in 10 volumes acetonitrile. The solution of free-based material in acetonitrile was then acetylated using 2.1 equivalents acetic anhydride and 2.5 equivalents triethylamine at room temperature for 1 hour. The crude material was concentrated and dissolved into ethyl acetate before being washed with saturated sodium bicarbonate and brine solutions. The washed organics were concentrated to dryness for a 73-75% yield with a purity of 93-97%.

Alternatively, and more efficiently, the Step 2, triethylamine after the free-basing was replaced with amberlyst-A21 for a total of 600 weight percent. The acetonitrile was increased to 15 volumes to facilitate agitation. After free-basing is complete, the acetic anhydride can be added at room temperature or below. Some impurities may be formed when reaction was performed at room temperature, as such, the reaction can be cooled to 0° C. to successfully reduce impurity formation. After reaction completion, the solution was previously concentrated to dryness. Typically, filterable solids may be preferred in certain isolation steps. As such, the acetonitrile solution was solvent-exchanged into ethyl acetate to yield filterable solids. These solids were filtered and washed with ethyl acetate before drying at 45° C. under vacuum for a 45% yield with a purity of 98%. The solvent-exchanged material can also be chilled to 0° C. for 1 hour to increase yield to 65% while achieving similar purity.

Typically, triethylamine is cheaper than amberlyst-A21, as such the reaction can also be accomplished using only triethylamine. This was achieved by cooling the mixture of L-cystine dimethylester dihydrochloride in 15 volumes acetonitrile to 0° C. before adding 4.2 equivalents of triethylamine followed by 2.1 equivalents of acetic anhydride. Previously, using amberlyst-A21 to free-base, the hydrochloride salt formed was bound to amberlyst-A21 and filtered off of the material to yield a clear colorless L-cystine dimethylester solution. Using triethylamine as free base led to the formation of triethylamine chloride salts. These were filtered off before salting out triethylamine using 0.5 N HCl in 13% NaCl solution. At this point, the reaction was solvent-exchanged into ethyl acetate and filtered similar to previous methods. The alternative method resulted in 88-92% yield with 93-95% purity.

Using only triethylamine for step 2 led to some loss of product before acid treatment, ineffective removal of triethylamine using acid, and degradation of material. When the triethylamine acetylation was first performed, solids were filtered before treating the solution. However, HPLC of the solids revealed the presence of desired product, Di-NACMe. Upon reaction completion, the slurry was now dissolved in 15 volumes ethyl acetate before treatment to maximize Di-NACMe in solution. Initially, 0.5 N HCl in 13% brine solution was used to treat the reaction solution. $^1$H-NMR results of acid-treated product revealed significant amounts of triethylamine were still present in step 2 product. In addition to the ineffective removal of triethylamine, the presence of acid in the material before drying degraded the material into a brown taffy when heat was applied. Since acid not only failed to remove triethylamine but also degraded material, acid was avoided. Saturated sodium bicarbonate replaced HCl to free-base triethylamine, acetic acid and HCl after reaction completion. After treating reaction solution with base to neutralize HCl, the belief was that triethylamine could be azeotroped with acetonitrile (ACN) while acetic acid stayed behind in ethyl acetate after the solvent-exchange.

The amidation of Di-NACMe into diNACA was performed in ammonium hydroxide. Initially, the solid was charged with at least 3 equivalents of 28-30% aqueous ammonium hydroxide. The solids dissolved in solution as diNACA precipitated. The slurry was agitated for 2 hours after solid formation before filtering and washing with minimal water. The solids were dried at 45° C. under vacuum. This method resulted in 60-70% yield with 70% purity. A solvent-exchange into ethanol after reaction completion further increased yield without sacrificing purity. higher purity of the diNACA can be used to achieve a higher yield in the final reduction step. Additionally, diNACA may be recrystallized from water to further enhance the purity.

The reduction of diNACA to NACA can be accomplished using tris (2-carboxyethyl)phosphine (TCEP), thioglycolic acid, and/or dithiothreitol (DTT). One reduction method uses 1.1 eq TCEP in 15 volumes 10:1 THF:water, heated to reflux. Reduction by thioglycolic acid was performed using 2.5 eq thioglycolic acid. The reaction was attempted using THF and ethanol as solvents. THF reaction yielded ~42% with a purity of 4%. Ethanol reaction had a yield of 2% with purity of 30%. With the goal of using ethanol, amberlyst-A21 and triethylamine were evaluated as bases to aid reduction. Amberlyst-A21 was determined to be a better base with yields of 45% and purity of 85%. Amberlyst-A21 also reduced reaction time from 2 days in triethylamine-mediated reactions to 3 hours in amberlyst-A21-mediated reactions. Alternatively, DTT can also be used. Various possible solvents can be used, e.g., dichloromethane (DCM), methanol, isopropanol, ethanol and/or other alcoholic solvents. Ethanol was chosen for its greater solubility of diNACA. The use of alternative reducing agents such as, but not limited to triphenylphosphine, TCEP, thioglycolic acid, etc., is contemplated herein as well as solvents such as, but not limited to, THF, EtOH, iPrOH, MeOH, DCM, water, etc. and bases, whether catalytic or stoichiometric, such as, but not limited to, Et3N, NaOH, amberlyst-A21, etc. Initially, to effect the reduction of the disulfide bond, 1.5 equivalents triethylamine were added to diNACA dissolved in ethanol followed by 1.5 equivalents of DTT. The solution was heated to reflux and held for 2 hours before solvent-exchanging into methyl tert-butyl ether to precipitate filterable solids. Further optimization of the reaction led to the reduction of triethylamine to a catalytic 0.1 equivalents, DTT to 1.25 equivalents and the reaction temperature to 62±3° C. with the effect of improving the impurity profile of the isolated NACA. This method yielded 85% of NACA with a purity of ≥98.0%. The purity of NACA may be further enhanced via recrystallization from ethanol.

These efforts to increase purity focused on the major impurities as measured by HPLC, namely, diNACA, DTT and cyclic DTT. Oxidation of NACA occurs when exposed to air. Ethanol and methyl t-butyl Ether (MTBE) used in the reduction and solvent-exchange were degassed in an effort to reduce diNACA. MTBE proved to be efficient in removing DTT and cyclic DTT, so an MTBE trituration was performed to improve purity.

diNACA purifications were performed with the goal of taking purer material through reduction for purer NACA.

Step 1: Formation of L-Cystine Dimethylester Dihydrochloride

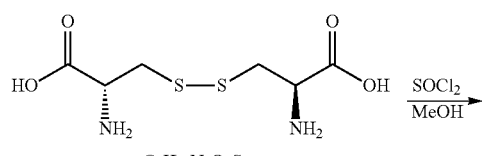

$C_6H_{12}N_2O_4S_2$
Mol Wt: 240.29
L-Cystine

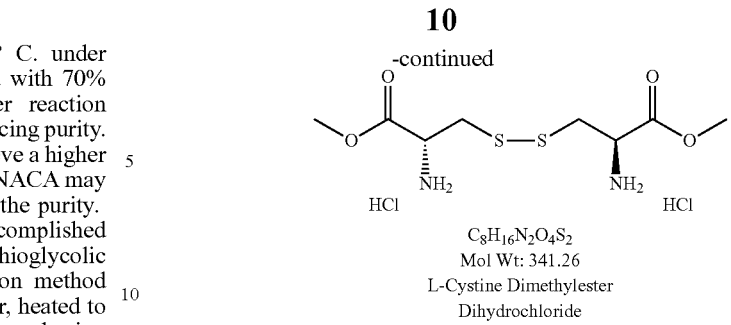

$C_8H_{16}N_2O_4S_2$
Mol Wt: 341.26
L-Cystine Dimethylester Dihydrochloride

| Reagents/Materials | MW | Density | Eqs. | Moles | Weight/ Volume |
|---|---|---|---|---|---|
| L-Cystine, ≥98.5% | 240.29 | — | 1.0 | 208 | 50 kg |
| Thionyl Chloride, ≥97% | 118.97 | 1.64 | 2.41 | 504 | 60 kg |
| Methanol (MeOH), ≥99% | 32.04 | 0.79 | 12.5 vol | — | 625 L |
| Methyl-tert Butyl Ether (MTBE), ≥99% | 88.15 | 0.74 | 8 vol | — | 400 L |

Set-up: A 2000 L glass-lined reactor;
50 kg L-Cystine; and
625 L Methanol was charged to the reactor and agitated while cooling to −10° C.
60 kg Thionyl Chloride was slowly added at ≤−5° C. After addition completion, the reaction material was heated to reflux and held for 16 hours. After the reaction was verified as complete by HPLC (≤0.5% starting material), the reaction was cooled to room temperature. The reaction mixture was concentrated to 6 volumes before solvent-exchanging into 3×8 volumes MTBE. The resulting slurry was agitated at room temperature for 1 hour before being filtered and washed with MTBE. The solids were dried at 45° C. under vacuum.
Yield: 68.15 kg (95.9%), Purity: 95.8%

Step 2: Formation of di-N-acetyl-1-cystine dimethylester (Di-NACMe)

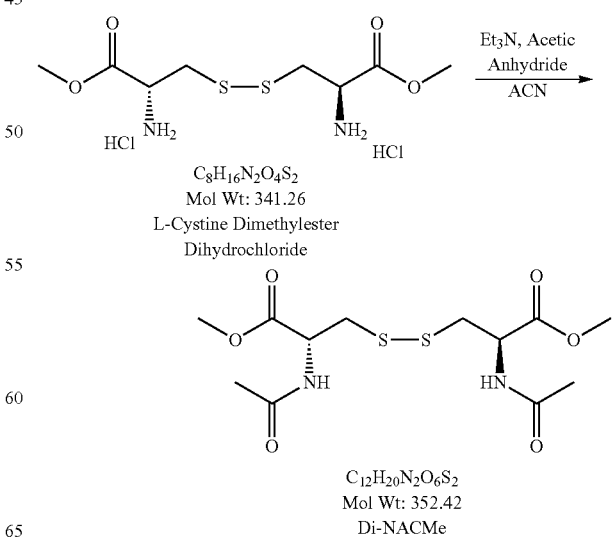

$C_8H_{16}N_2O_4S_2$
Mol Wt: 341.26
L-Cystine Dimethylester Dihydrochloride $C_{12}H_{20}N_2O_6S_2$
Mol Wt: 352.42
Di-NACMe

| Reagents/Materials | MW | Density | Eqs. | Moles | Weight/Volume |
|---|---|---|---|---|---|
| L-Cystine Dimethylester Dihydrochloride, ≥95% | 341.26 | — | 1.0 | 76.2 | 26 |
| Acetonitrile, ≥99% | 41.05 | 0.79 | 23 vol | — | 472 |
| Triethylamine (TEA), ≥99% | 101.19 | 0.73 | 4.2 | 316.2 | 32 |
| Acetic Anhydride, ≥99% | 102.09 | — | 2.1 | 156.7 | 16 |
| Ethyl Acetate, ≥99% | 88.1 | — | 41 vol | — | 958 |

Set-up: A 800 L glass lined reactor 26 kg L-Cystine Dimethylester Dihydrochloride and 390 L Acetonitrile (ACN) is charged to the reactor and agitated while cooling to 0° C.

32 kg Triethylamine is added to the reactor at ≤5° C.

16 kg Acetic Anhydride is slowly added to the reactor at ≤5° C. Upon addition completion the reaction is held for 30 minutes at 5±5° C. After reaction was verified as complete by HPLC (≤0.5% starting material), 10 volumes ethyl acetate was charged to the reactor and agitated to ambient. The resulting reaction mixture was washed with 2×2 volumes saturated bicarbonate. The aqueous layer was back extracted with 5 volumes ethyl acetate. All organics were combined and dried over sodium sulfate and polish filtered. The filtrate was concentrated to 5 volumes before azeodrying with 2×4 volumes acetonitrile followed by a solvent-exchange into 4×6 volumes ethyl acetate. The resulting slurry was agitated at 0° C. for 1 hour before being filtered and washed with 2 volumes ethyl acetate. The solids were dried at 25° C. under vacuum.

Average Yield: 29.56 kg (100%), Average Purity: 92.2%

Step 3: Formation of DiNACA

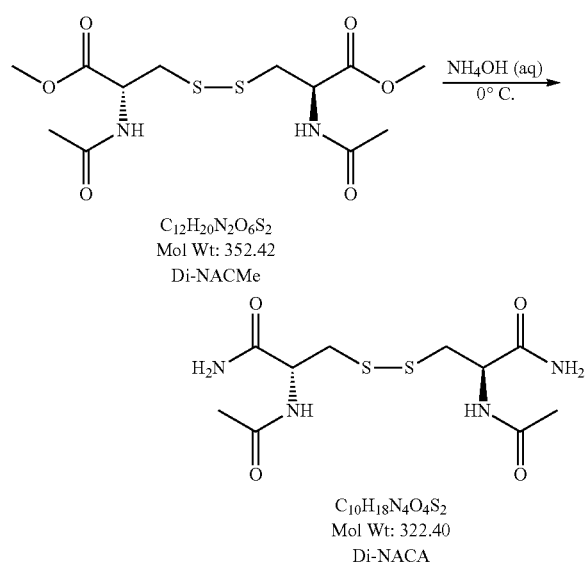

| Reagents/Materials | MW | Density | Eqs. | Moles | Weight/Volume |
|---|---|---|---|---|---|
| Di-NACMe | 352.42 | — | 1.0 | 247 | 87.05 kg |
| 28-30% Ammonium Hydroxide | 35.05 | 0.9 | 8.44 | 2088 | 244 kg |

| Reagents/Materials | MW | Density | Eqs. | Moles | Weight/Volume |
|---|---|---|---|---|---|
| Ethanol, absolute 200 proof | 46.07 | 0.79 | 17 vol | — | 1483 L |

Set-up: A 800 L glass lined reactor 244 kg Degassed 28-30% NH₄OH (aq) was cooled to 0° C. before 87.05 kg Di-NACMe was charged to the reactor and agitated for 4 hours. After reaction was verified as complete by HPLC (≤0.5% starting material), the reaction mixture was solvent-exchanged into 3×5 volumes degassed ethanol. The resulting slurry was agitated at 0° C. for 30 minutes before being filtered and washed with cold degassed ethanol. The solids were dried at 45° C. under vacuum.

Average Yield: 52 kg (67.1%), Average Purity: 72.0%

Step 3A: Purification of DiNACA

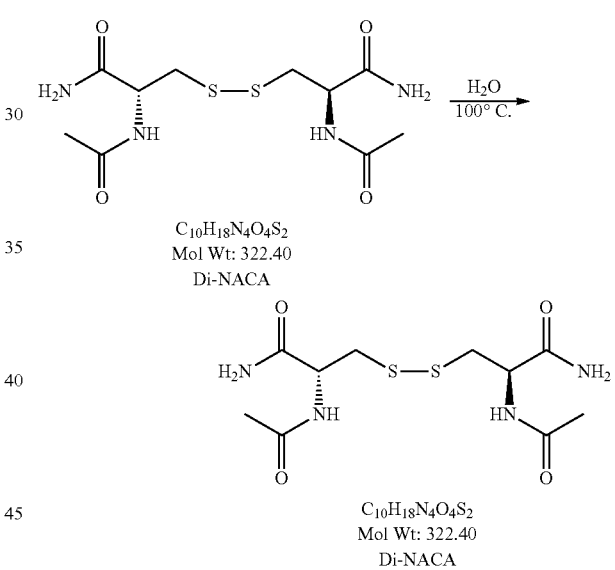

| Reagents/Materials | MW | Density | Eqs. | Moles | Weight/Volume |
|---|---|---|---|---|---|
| DiNACA | 322.40 | — | 1.0 | 161 | 52 kg |
| Process Water, Filtered | 18.02 | 1.0 | 8 vol | — | 416 L |
| DiNACA | 322.40 | — | 1.0 | 161 | 52 kg |
| Process Water, Filtered | 18.02 | 1.0 | 8 vol | — | 416 L |

Set-up: A 800 L glass lined reactor 52 kg DiNACA and

416 L Degassed Water were charged to the flask and agitated while heating to reflux. Upon dissolution, the reaction solution was allowed to cool overnight. The solids were filtered and washed with 2 volumes cold degassed water. The solids were dried at 45° C. under vacuum.

Recovery: 36 g (69%), Purity: 86.4%

Step 4: Formation of NACA

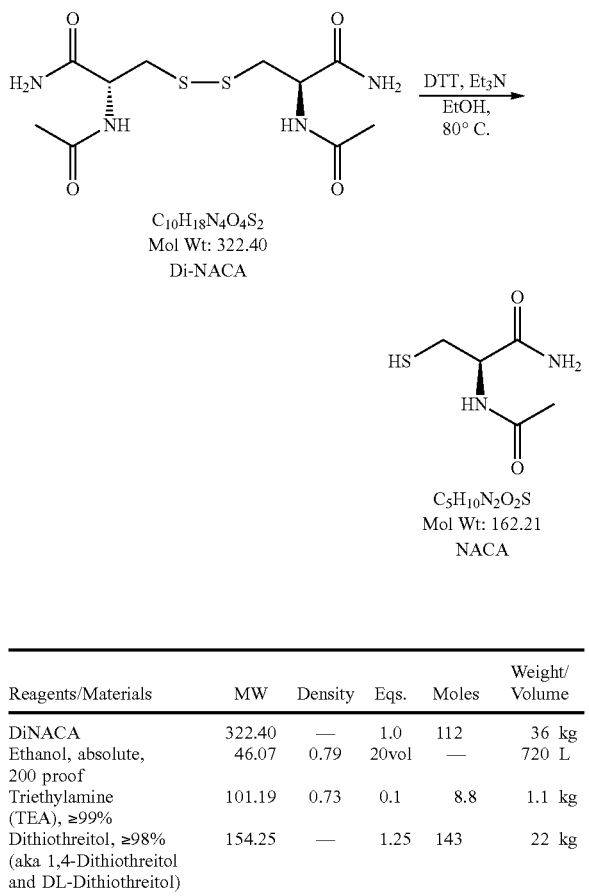

| Reagents/Materials | MW | Density | Eqs. | Moles | Weight/Volume |
|---|---|---|---|---|---|
| DiNACA | 322.40 | — | 1.0 | 112 | 36 kg |
| Ethanol, absolute, 200 proof | 46.07 | 0.79 | 20vol | — | 720 L |
| Triethylamine (TEA), ≥99% | 101.19 | 0.73 | 0.1 | 8.8 | 1.1 kg |
| Dithiothreitol, ≥98% (aka 1,4-Dithiothreitol and DL-Dithiothreitol) | 154.25 | — | 1.25 | 143 | 22 kg |

Set-up: A 800 L glass lined reactor
720 L Degassed Ethanol,
1.1 kg Triethylamine,
22 kg Dithiothreitol and
36 kg of DiNACA were charged to the reactor before heating the reaction to 62±3° C. The reaction is held at temp for 2 hours. After reaction was verified as complete by HPLC (≤0.5% starting material on overloaded column), cool reaction to ambient. The reaction solution was polish filtered and concentrated to 10 volumes before solvent exchanging into 4×10 volumes degassed MTBE. The resulting slurry was agitated overnight before being filtered and washed with 2 volumes degassed MTBE. The solids were dried @ 45° C. under vacuum. diNACA was recrystallized with ethanol.

Yield: 27.8 kg (77.2%), Purity: 98.5%

Figure 3:
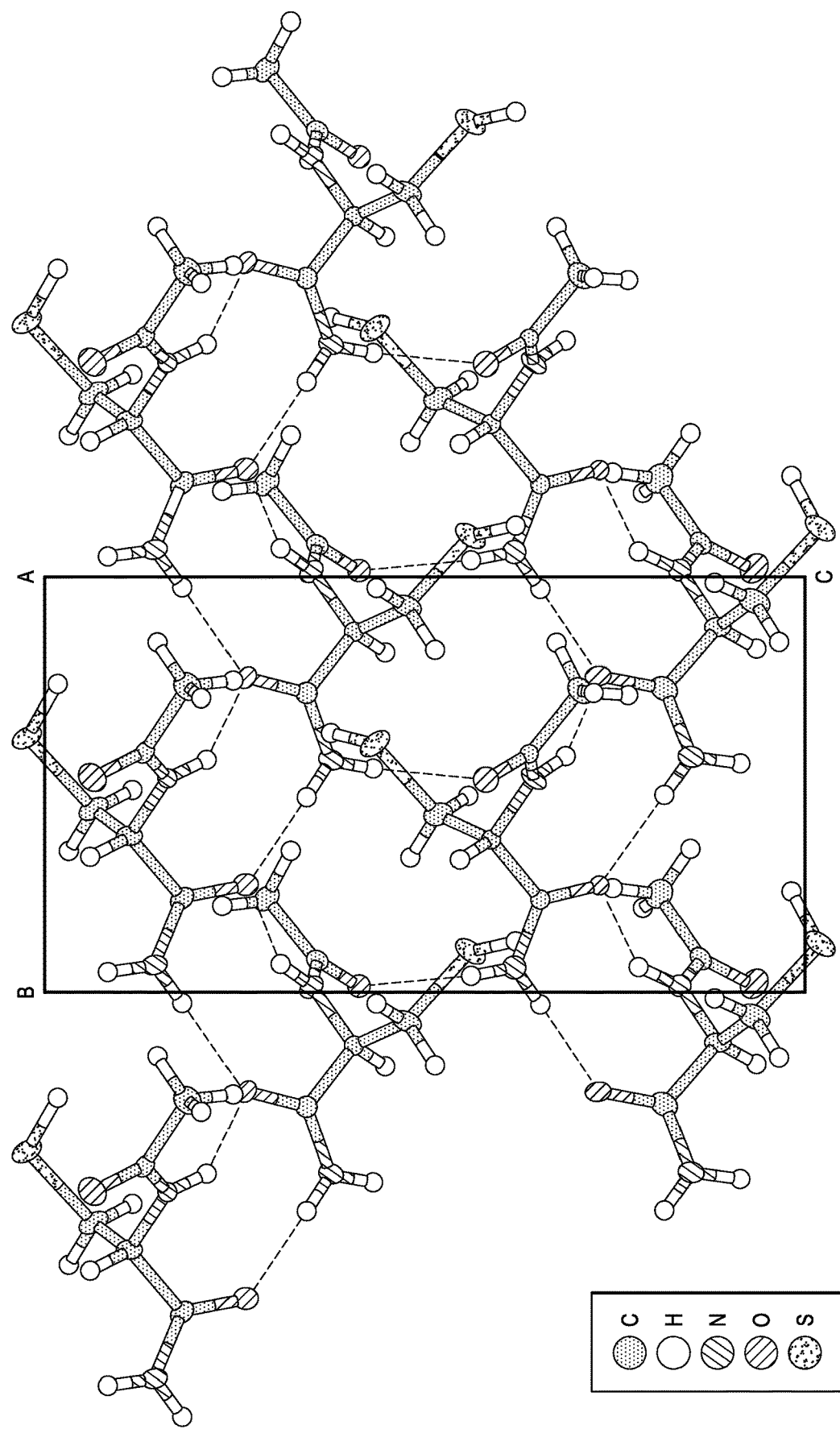
FIG. 3 shows a view of a unit cell an axis of NPI-001 containing complete molecules. All atoms are shown with thermal ellipsoids set at the 50% probability level. Color code: Carbon, grey; H, white; O, red; S, yellow.
Figure 5:
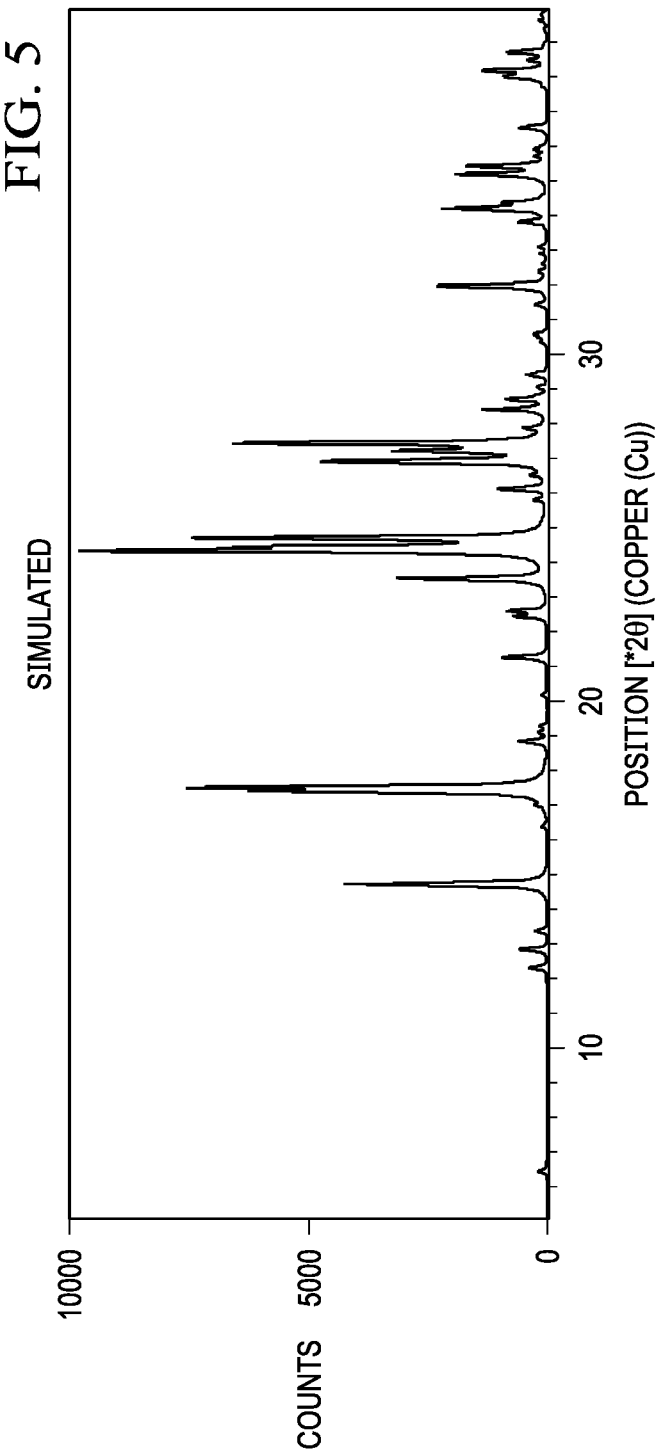
FIG. 5 shows Simulated (120 K) XRPD 2θ diffractogram of NPI-001.
Figure 6:
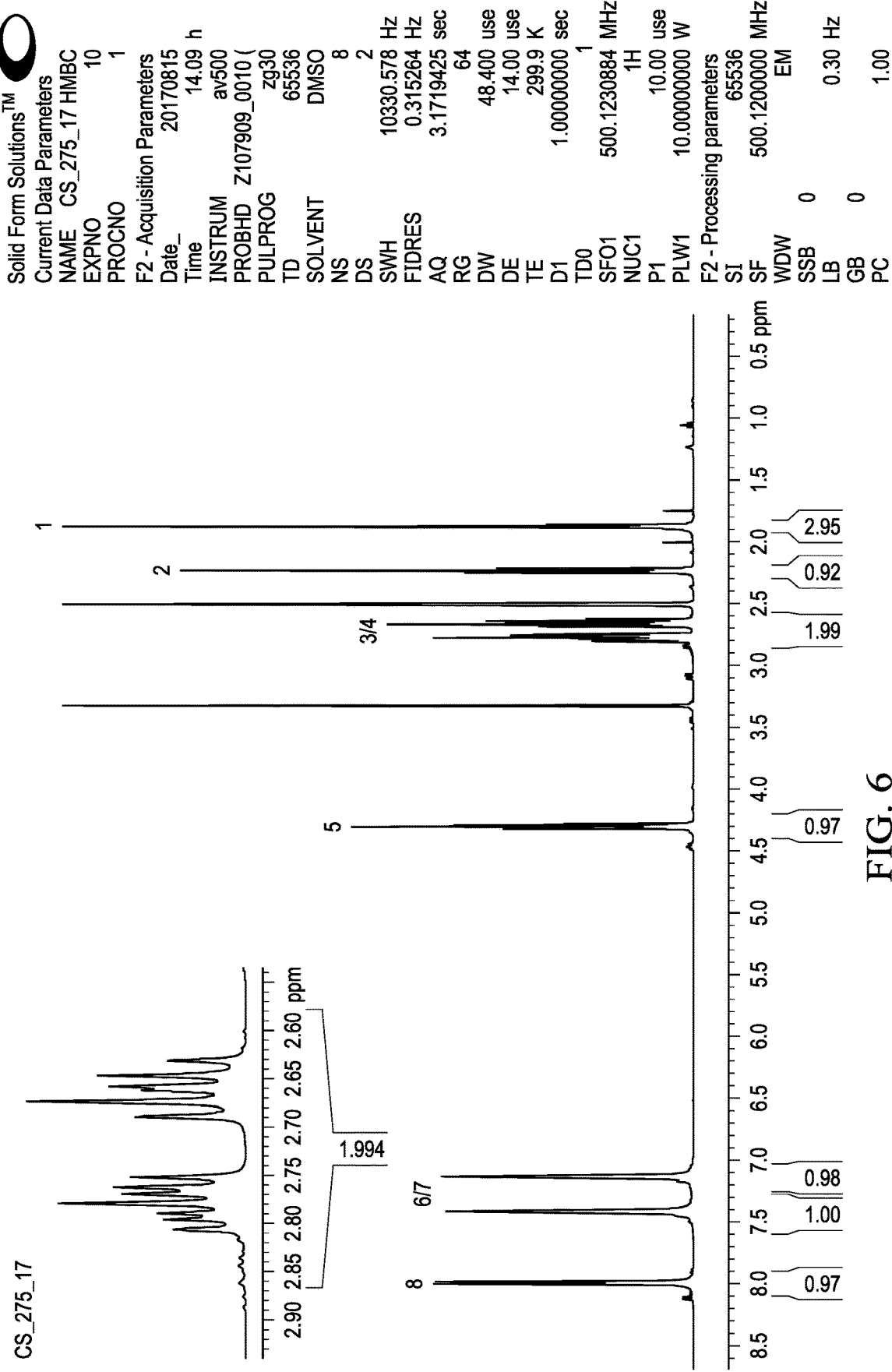
FIG. 6 shows $^1$H-NMR of NACA.
Figure 7:
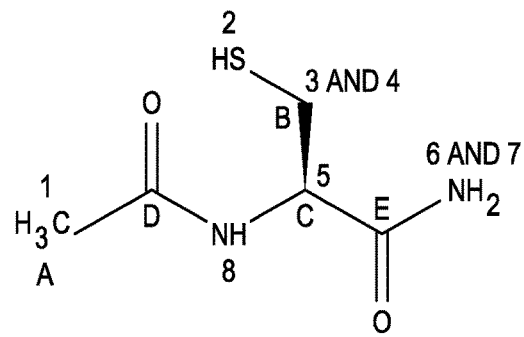
FIG. 7 shows $^1$H-NMR assignments for NACA ($^1$H and $^{13}$C assignments are based on analysis of the 1D $^1$H NMR, $^1$H-$^{13}$C HSQC and $^1$H-$^{13}$C HMBC spectra.)
Figure 8:
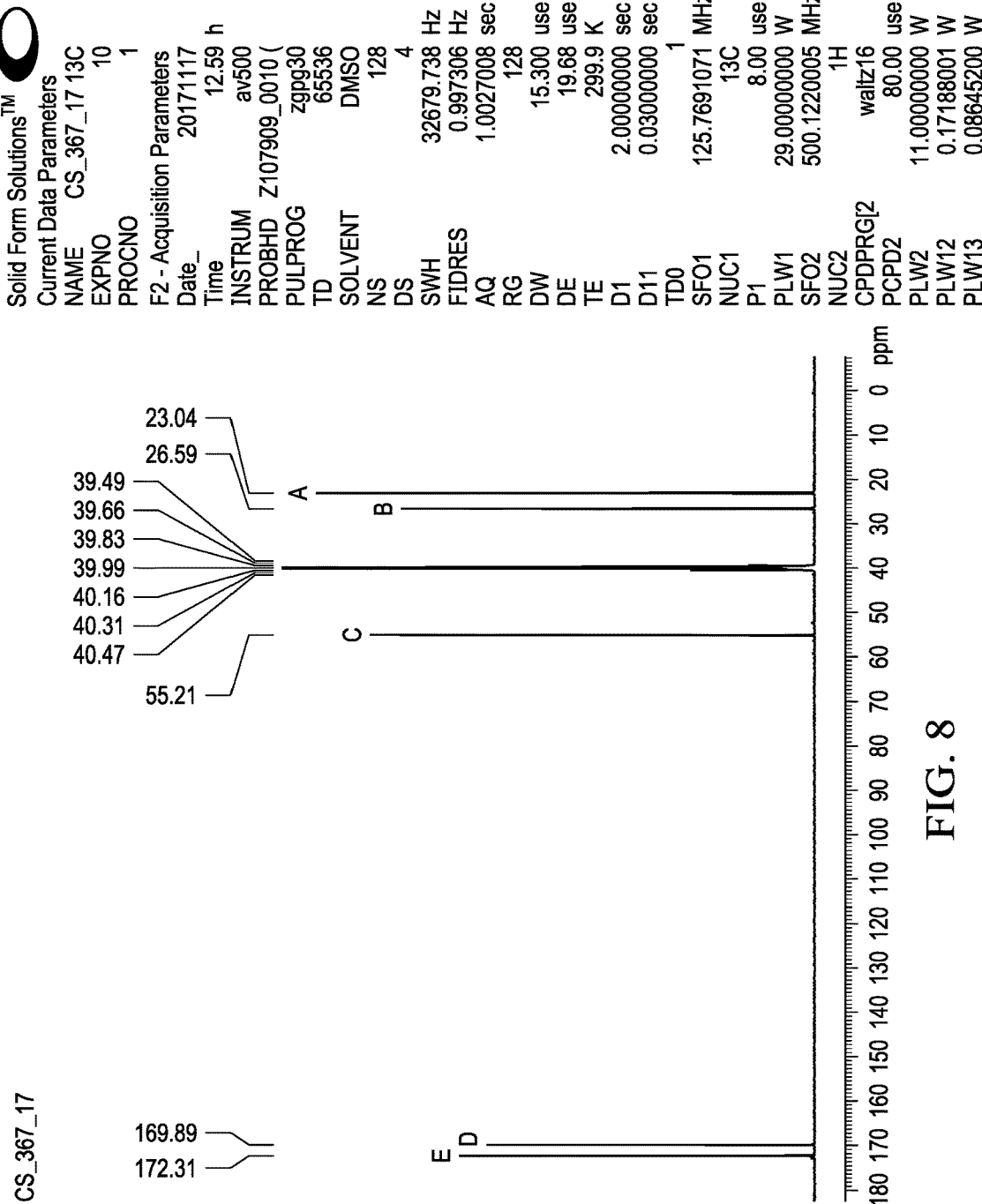
FIG. 8 shows $^{13}$C-NMR of NACA.
Figure 9:
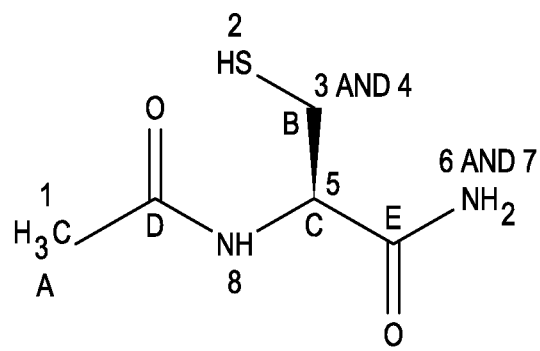
FIG. 9 shows $^{13}$C-NMR assignments for NACA. ($^1$H and $^{13}$C assignments are based on analysis of the 1D $^1$H NMR, $^1$H-$^{13}$C HSQC and $^1$H-$^{13}$C HMBC spectra).
Figure 10:
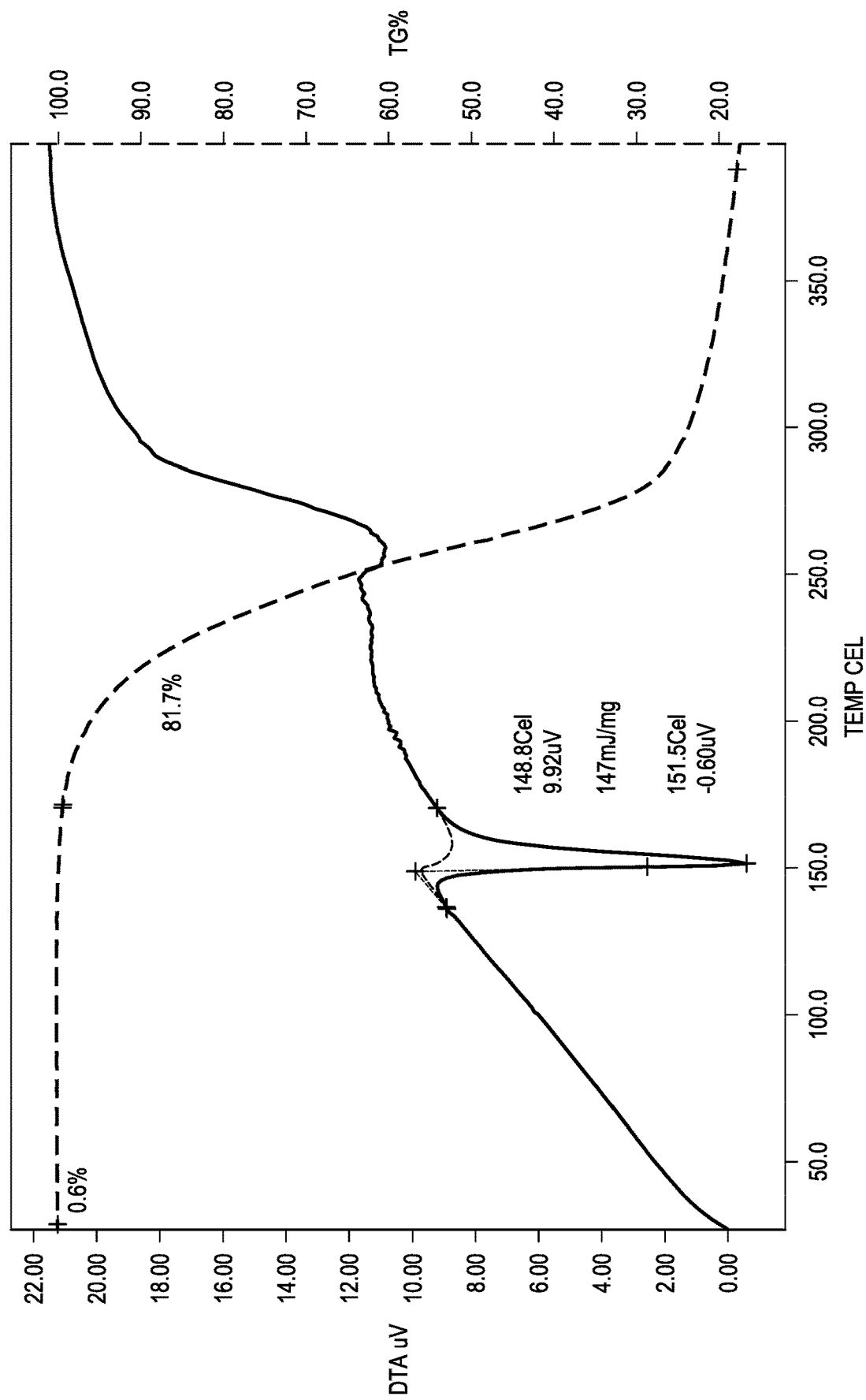
FIG. 10 shows combined thermogravimetry/differential scanning calorimetry scans of NACA.
Figure 11:
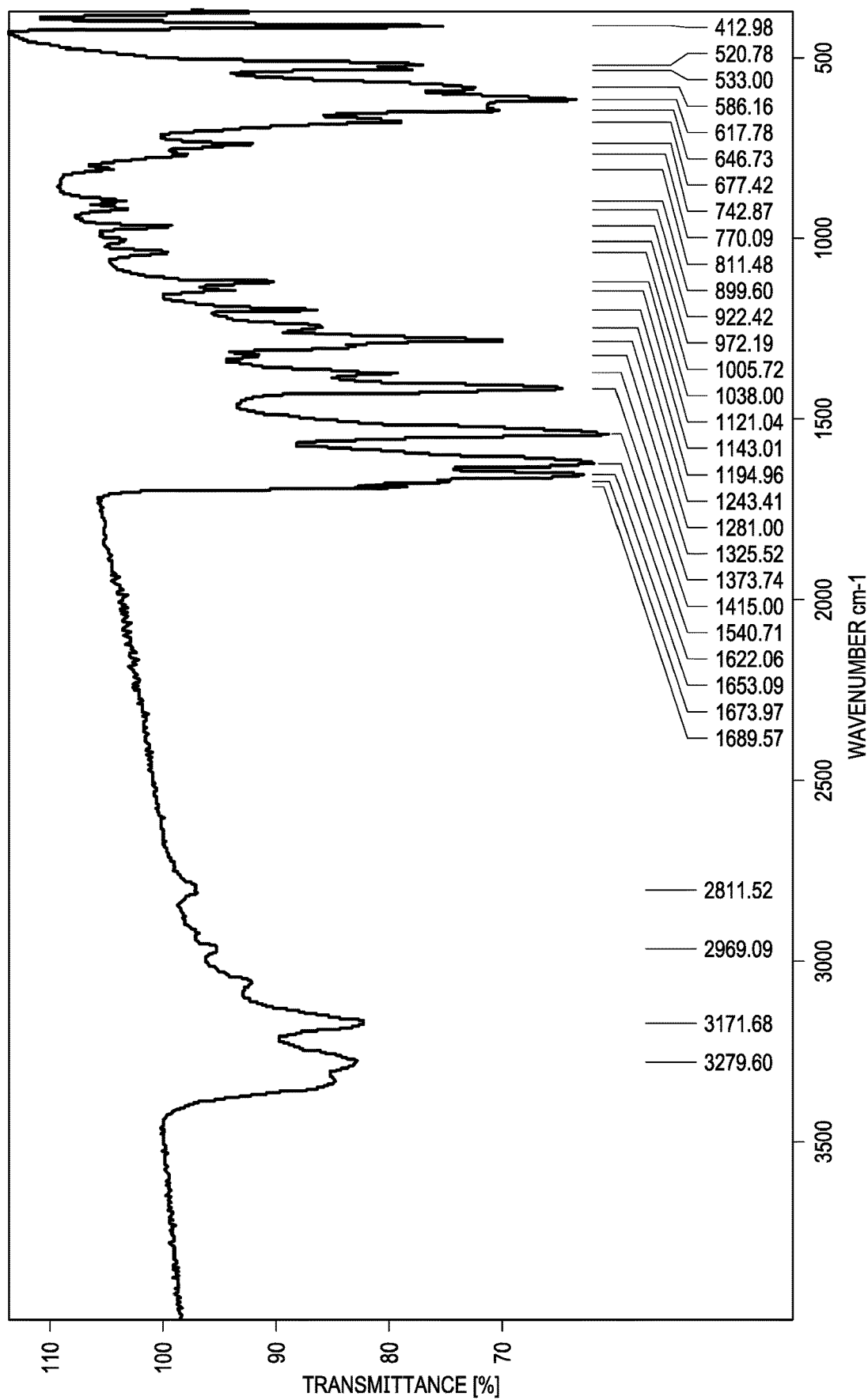
FIG. 11 shows fourier transform-infrared (FT-IR) spectrum of NACA.

FIG. 1 shows a basic chemical synthesis of the present invention. FIG. 2A shows a view of NPI-001 molecule 'A' without atom labeling. All non-hydrogen atoms are shown with thermal ellipsoids set at the 50% probability level. Color code: Carbon, grey; H, white; O, red; S, yellow. FIG. 2B shows a portion of NACA derived from starting material L-Cystine. FIG. 3 shows a view of unit cell an axis of NPI-001 containing complete molecules. All atoms are shown with thermal ellipsoids set at the 50% probability level. Color code: Carbon, grey; H, white; O, red; S, yellow. FIG. 4 shows results of liquid chromatography with mass spectrometric detection. FIG. 5 shows Simulated (120 K) XRPD 2θ diffractogram of NACA. FIG. 6 shows $^1$H-NMR of NACA. FIG. 7 shows $^1$H-NMR assignments for NACA ($^1$H and $^{13}$C assignments are based on analysis of the 1D $^1$H NMR, $^1$H-$^{13}$C HSQC and $^1$H-$^{13}$C HMBC spectra.). FIG. 8 shows $^{13}$C-NMR of NACA. FIG. 9 shows $^{13}$C-NMR assignments for NACA. ($^1$H and $^{13}$C assignments are based on analysis of the 1D $^1$H NMR, $^1$H-$^{13}$C HSQC and $^1$H-$^{13}$C HMBC spectra). FIG. 10 shows combined thermogravimetricy/differential scanning calorimetry scans of NACA. FIG. 11 shows fourier transform-infrared spectrum (FT-IR) of NACA.

Analytical procedures for NACA. The analytical methods for the testing of NACA drug substance are listed in Table 5. Most of the methods are USP compendial tests. The additional NACA drug substance methods (which are not compendial) include two HPLC methods for assay and impurities, and one chiral HPLC method for chiral purity. Each of the non-compendial methods is described in more detail in sections that follow.

TABLE 5

List of Analytical Procedures for NACA Drug Substance

| Test | Test Method | Description |
|---|---|---|
| Appearance | Visual | A sample of the solid material is examined visually for form and color. |
| ID-1 | IR | Method follows USP<197A> |
| ID-2 | $^1$H-NMR | Method follows USP<761> |
| Potency/Assigned Purity | Calculated | Purity = (100 − % HPLC impurities − % H$_2$O − % ROI − % Total Residual Solvents) |
| Organic | HPLC-Method I | Reverse phase gradient HPLC method. |
| Impurities/Related Substances | HPLC Method II | Reverse phase gradient HPLC method. |
| Chirality | Optical Rotation | Method follows USP<781> (c 1.00, MeOH) |
| Chiral Purity | Chiral HPLC | Chiral HPLC method |
| Residue on Ignition | USP<281> | Method follows USP<281> |
| DSC | USP<891> | Method follows USP<891> |
| X-ray Powder Diffraction | USP<941> | Method follows USP<941> |
| Heavy Metals | USP<233> | Method follows USP<233> |
| Residual Solvents | GC (USP<467>) | Method follows USP<467> |
| Water Content | Karl Fischer | Method follows USP<921> version 1c |
| Microbial Limits | Microbial enumeration | Method follows USP<61> |
|  | Test for specified organisms | Method follows USP<62> |

HPLC Method for Purity and Related Substances. Analysis of the NACA drug substance for purity and related substances makes use of a reverse phase HPLC with an ultraviolet (UV) detector. The method is summarized in Table 6. This method is also used as the in-process method for each step to follow completion of reaction.

TABLE 6

Summary of NACA HPLC Method I (Purity and Related Substances)

| Method Element | Description |
|---|---|
| Column | Phenomenex Synergi Hydro-RP, 4.6 × 250 mm, 4 µm |
| Detection | 214 nm |

TABLE 6-continued

Summary of NACA HPLC Method I (Purity and Related Substances)

| Method Element | Description | | |
|---|---|---|---|
| Column Temperature | 40° C. | | |
| Injection Volume | 25 μL | | |
| Flow Rate | 1.0 mL/minute | | |
| Mobile Phase A | 0.02% $H_3PO_4$ in $H_2O$ | | |
| Mobile Phase B | Acetonitrile (ACN) | | |
| Gradient | Time (min) | % A | % B |
| | 0.0 | 100 | 0 |
| | 15.0 | 90 | 10 |
| | 25.0 | 0 | 100 |
| | 30.0 | 0 | 100 |
| | 30.1a | 100 | 0 |
| | 35.0 a | 100 | 0 |
| System Suitability | (a) Equilibration time-no integration<br>1. Specificity: No significant interference in the blank chromatogram at retention times of interest.<br>2. The S/N of the NACA peak in the 0.03% sensitivity solution must be ≥10<br>3. The % RSD of the RT and peak area of NACA in the 5 injections of the first sample must be ≤2.0%.<br>4. The recovery of one standard prep (average of all injections) versus a second standard prep (average of all injection) must be 100.0 ± 2.0%. | | |

Figure 12:
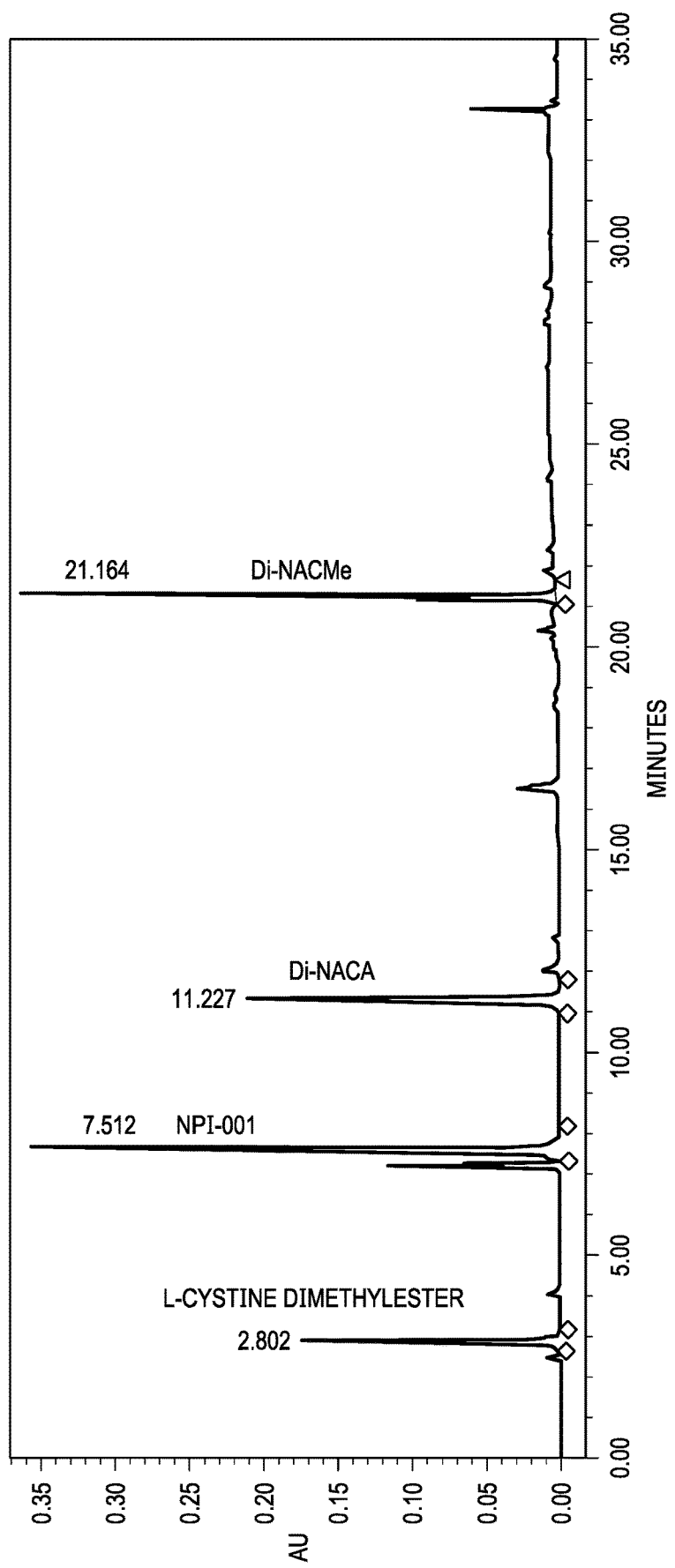
FIG. 12 is a representative Method-I Chromatogram showing NACA, Intermediates and Starting Material.

FIG. 12 shows a Method I Chromatogram Showing NACA and all Intermediates and Starting Material.

HPLC Method for Impurities B1 and B2. Method-I did not always detect impurities B1 and B2. A second method, Method-II, was developed to reliably quantitate these two impurities. The method is summarized in Table 7. A representative chromatogram showing the retention times of B1 and B2 is presented in FIG. 13.

TABLE 7

Summary of NACA HPLC Method II (Impurities B1 and B2)

| Method Element | Description | | |
|---|---|---|---|
| Column | Agilent Zorbax SB-Aq, 4.6 × 250 mm, 5 μm | | |
| Detection | 214 nm | | |
| Column Temperature | 40° C. | | |
| Injection Volume | 25 μL | | |
| Flow Rate | 1.0 mL/minute | | |
| Mobile Phase A | 0.02% $H_3PO_4$ in $H_2O$ | | |
| Mobile Phase B | Acetonitrile (ACN) | | |
| Gradient | Time (min) | % A | % B |
| | 0.0 | 100 | 0 |
| | 5.0 | 100 | 0 |
| | 20.0 | 0 | 100 |
| | 25.0 | 0 | 100 |
| | 25.01 | 100 | 0 |
| | 35.0 | 100 | 0 |
| System Suitability | 1. Specificity: No significant interferences in the blank chromatogram at retention times of interest.<br>2. The S/N of the NACA peak in the 0.03% sensitivity solution must be ≥10<br>3. The % RSD of the RT and peak area of NACA in the 5 injections of the first sample must be ≤2.0%. | | |

Figure 13:
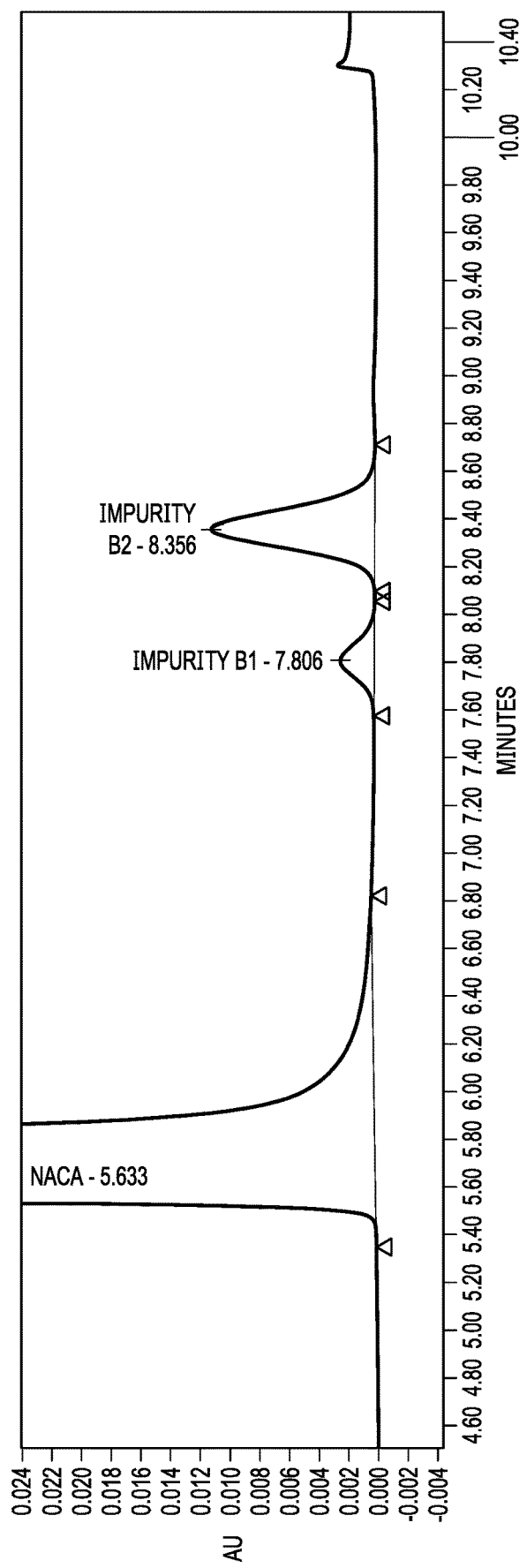
FIG. 13 is a representative Chromatogram of Method-II Showing B1 and B2.

FIG. 13 is a representative Chromatogram of Method-II Showing B1 and B2

Chiral HPLC Method for Measuring Chiral Purity of NACA. A chiral method was developed to assess the chiral purity of NACA. The method is summarized in Table 8.

TABLE 8

Summary of Chiral HPLC Method for NACA

| Method Element | Description |
|---|---|
| Column | Diacel Chiralpak IC-3, 4.6 × 150 mm |
| Detection | 217 nm |
| Column Temperature | 35° C. |
| Injection Volume | 20 μL |
| Flow Rate | 0.8 mL/minute |
| Mobile Phase (isocratic) | 0.05% $H_3PO_4$ in 1:1 n-hexane:IPA |
| System Suitability | 1. Specificity: No significant interferences in the blank chromatogram at retention times of interest.<br>2. The resolution between the enantiomers is sufficient to allow for accurate integration of both peaks.<br>3. The S/N of the NACA peak in the 0.03% sensitivity solution must be ≥10<br>4. The % RSD of the RT and peak area of NACA in the 6 injections of the first sample must be ≤2.0%. |

Figure 14:
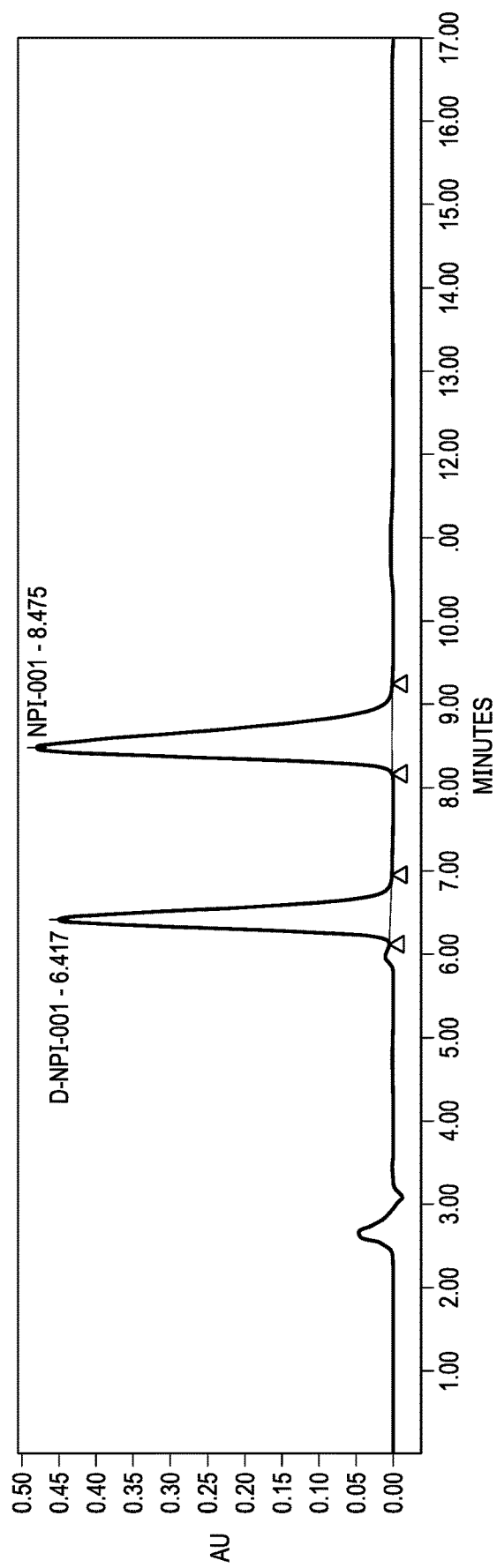
FIG. 14 is a representative chromatogram showing separation of R-NACA and S-NACA.

FIG. 14 is a chromatogram Showing Separation of R-NACA and S-NACA.

Preparation of D-NACA. D-Cystine was obtained from a commercial vendor. D-Cystine was dissolved in water and pH was adjusted to pH 9-10 with NaOH. Acetic anhydride was added dropwise at 0° C. and pH maintained at 9-10. Solution was stirred for 4 hours after which it was acidified to pH~2 with HCl. The solvent was evaporated under reduced pressure. 20 mL MeOH was added to the flask to dissolve contents. Solution was filtered. Filtrate was concentrated and evaporated. Thin layer chromatography (MeOH:DCM:HOAc, 1:8:1) indicated loss of starting material and appearance of a single new peak for D-acetylcystine. D-Acetylcystine was charged to a round-bottomed flask with 50 mL MeOH to which was added 0.35 mL concentrated $H_2SO_4$ via syringe, dropwise, at ambient temperature, with agitation. Solution turned turbid. IPC by TLC (MeOH:DCM, 1:9] showed no starting material. Solvent was evaporated. Fraction was neutralized with NaHCO3 (saturated), extracted with DCM (50 ml twice), washed with water, dried over Na2SO4, filtered, purged with nitrogen and concentrated under reduced pressure to yield a net weight of 7.8 g white solid, formed in the refrigerator. N-acetylcysteine methyl ester was charged into a 3-necked, round-bottomed flask with nitrogen bubbler, and magnetic stirrer. Ammonium hydroxide at ambient temperature was added and purged with nitrogen through reaction mixture and agitated at ambient temperature. Solvent was evaporated under vacuum and a white solid formed. Ethanol was added and heated to form clear solution and left to stand overnight. White solid crystallized, was filtered, washed with ethanol and purified by column chromatography.

Oral Solution of NACA.

A study was conducted to determine the solubilization of NACA in ORA-SWEET® (Ora-Sweet is a commercially available syrup vehicle containing water, sucrose, glycerin, sorbitol, flavoring, buffering agents (citric acid and/or sodium phosphate), methyl paraben and potassium sorbate, pH 4.2 manufactured by Paddock Laboratories, Inc., Minneapolis, Minn.). HPLC equipment and glass containers and stirrers were utilized.

NACA at 80 mg/ml did not readily dissolve in ORA-SWEET, rather it required stirring for 20-30 minutes to achieve a solution. However, NACA was readily dissolved in water with shaking for 30 seconds, followed by dilution with an equal volume of ORA-SWEET with shaking for 20-30 seconds. Therefore, NACA was dissolved in 50 mL water followed by 50 mL Ora-Sweet, shaken to dissolve in an opaque plastic bottle with closure and provided to subject for self-administration (oral ingestion).

NACA oral solution was also be prepared as 100 ml oral solution in ORA-SWEET. Doses can be achieved ranged from 250 mg to 4000 mg/day/patient. The NACA dissolution in water followed by dilution with ORA-SWEET was found optimal for compounding. ORA-SWEET is a pale pink solution with a cherry syrup flavor. NACA has a mild sulfur odor and a bitter taste (like burned sesame seeds). When dissolved in ORA-SWEET, the odor and taste were masked.

The following instructions for preparation of NACA Oral Solution were developed:

Weigh NACA [either 250, 750, 1500, 3000 or 4000 mg (±1 mg), as appropriate for the particular dose group] and place into a 125 mL (approximately) capacity opaque high density polyethylene, labeled (see Table 9) bottle with opaque polypropylene screw cap.

TABLE 9

Container/closure for NACA Oral Solution Used for Phase 1 Study

| Component | Description |
|---|---|
| Bottle | 125 mL opaque white high density polyethylene bottle |
| Cap | Polypropylene opaque white cap |
| Label | Pharmacy approved label |

Measure 50 mL of Purified Water and pour into each bottle containing NACA and shake vigorously by hand (at least 30 seconds) to dissolve.

Measure 50 mL Ora-Sweet and pour into each bottle containing NACA and shake vigorously by hand (at least 30 seconds) to dissolve.

A subject drinks entire solution, followed by two 20-ml rinses of the container with water, which are also drank.

Tablet or Capsule of NACA for clinical phase 1 or clinical phase II trials:

The qualitative composition for NACA Tablets is presented in Table 10.

TABLE 10

Qualitative Composition of NACA Tablets

| Component | Quality Standard |
|---|---|
| NACA | Nacuity |
| Lactose | NF |
| Microcrystalline Cellulose | NF |
| Croscarmellose Sodium | NF |
| Stearic acid | NF |

NACA Tablets, 250 mg, are formulated as an immediate release drug product. A roller-compacted blend containing 250 mg NACA is compressed into round, biconvex tablets.

The formulation use to manufacture NACA Tablets is a roller compacted blend of common excipients (Table 11). The blend is compressed into round, biconvex shaped tablets.

TABLE 11

Quantitative Composition of NACA Tablets

| Component | mg/tablet weight | % | Function | Quality Standard |
|---|---|---|---|---|
| NACA | 250.0 | 50 | Drug substance | Nacuity |
| Lactose | 42.875 | 8.575 | Filler | NF |
| Microcrystalline Cellulose | 177.125 | 35.425 | Filler | NF |
| Croscarmellose Sodium | 25 | 5.0 | Disintegrant | NF |
| Stearic acid | 5 | 1.0 | Lubricant | NF |
| TABLET WT | 500 | 100 | — | — |

Type of Container and Closure for Dosage Form

NACA Tablets, 250 mg, are packaged in high density polyethylene (HDPE) bottles with foil induction seal and a white polyproplylene screw-top closure. Excipients used for the formulation meet compendial standards. Lactose functions as a filler. Microcrystalline cellulose functions as a filler. Croscarmellose Sodium functions as a disintegrant. Stearic Acid functions as a lubricant. Excipients were screened by assessing the stability of NACA in mixtures with each excipient. Mixtures of NACA with either microcrystalline cellulose, lactose monohydrate, croscarmellose sodium and crospovidone/Kollidon CL and hydroxypropyl cellulose exhibited less degradation of NACA compared to other excipients (Table 12). Hydroxypropyl cellulose exhibited greater levels of impurities than the other lead excipients (data not shown). Based on these results as well as the collective experience of the Formulators, microcrystalline cellulose, lactose monohydrate, croscarmellose sodium and steric acid were chosen as excipients for NACA Tablets.

TABLE 12

Stability results for NACA/excipient mixtures after 4 weeks at 40° C./75% RH

| Sample ID | Excipient | Ratio of API:Excipient | % Assay |
|---|---|---|---|
| SPt: 17004Q4; P | NA | 1:0 | 95.3 |
| SPL-1700405-P | Microcrystalline Cellulose PH 102 | 1:1 | 94.9 |
| SPL-1700406-P | Lactose Monohydrate (Fastflo) | 1:1 | 93.2 |
| SPL-1700407-P | Croscarmellose Sodium | 4:1 | 93.6 |
| SPL-1700408-P | Crospovidone/Kollidon CL | 4:1 | 94.4 |
| SPl-1700409-P | Sodium Lauryl Sulfate | 4:1 | 26.2 |
| SPL-1700410-P | Colloidal Silicon Dioxide | 4:1 | 92.7 |
| SPL-1700411-P | Magnesium Stearate | 9:1 | 77.5 |
| SPL-1700412-P | Sodium Stearyl Fumarate | 9:1 | 86.7 |

Tables 13 and 14 were prepared. The use of roller compaction of formulations of NACA with various excipients yielded powders with acceptable flow properties. Roller compaction followed by compression yielded tablets with acceptable properties based on friability and hardness. The clinical formulation was selected based on acceptable 2-week stability data.

Dry blending of formulations of NACA with various excipients yielded poorly flowing powders. Dry blending followed by compression yielded tablets that were unsatisfactory based on friability and hardness.

The use of roller compaction of formulations of NACA with various excipients yielded powders with acceptable flow properties. Roller compaction followed by compression yielded tablets with acceptable properties based on friability and hardness.

TABLE 13

Finished Prototype NACA Tablets by Roller Compaction

| Batch Formulation | Product Batch # | Packaging Configurations* |
|---|---|---|
| NAC1G50%0401 | NAC1T250mg0401A | 1 |
| Low Roller Compaction | NAC1T250mg0401B | 2 |
| Force (3 kN) | | |
| NAC1G50%0402 | NAC1T250mg0402A | 1 |
| High Roller Compaction | NAC1T250mg0402B | 2 |
| Force (6 kN) | | |
| NAC1G50%0501 | NAC1T250mg0501A | 1 |
| Low Roller Compaction | NAC1T250mg0501B | 2 |
| Force (3 kN) | | |
| NAC1G50%0502 | NAC1T250mg0502A | 1 |
| High Roller Compaction | NAC1T250mg0502B | 2 |
| Force (6 kN) | | |

*Packaging Configuration 1 (With Desiccant):
Bottle: 60 CC 33/400 W-HDPE ROUND BTL
Cap: 33 mm SECURX with SG-75M liner
Desiccant: Desiccant Canister Silica Gel 2GM
Fill: 20 tablets per bottle
*Packaging Configuration 2 (Without Desiccant):
Bottle: 60 CC 33/400 W-HDPE ROUND BTL
Cap: 33 mm SECURX with SG-75M liner
Fill: 20 tablets per bottle

TABLE 14

NACA Tablet Prototype Batch Formulations by Roller Compaction

| Component | NAC1G50%0401 mg/tablet weight Low Force | | NAC1G50%0402 mg/tablet weight High Force | | NAC1G50%0501 mg/tablet weight Low Force | | NAC1G50%0502 mg/tablet weight High Force | |
|---|---|---|---|---|---|---|---|---|
| | g | % | g | % | g | % | g | % |
| INTRAGRANULAR | | | | | | | | |
| NACA | 750 | 50 | 750 | 50 | 750 | 50 | 0 | 0 |
| NACA Direct Blend 70% (NAC1B70%01) | 0 | 0 | 0 | 0 | 0 | 0 | 0 | 71.42 |
| Lactose | 330 | 22 | 330 | 22 | 128.6 | 8.57 | 857.0 | 0 |
| Microcrystalline Cellulose | 330 | 22 | 330 | 22 | 128.6 | 8.57 | 0 | 0 |
| Croscarmellose Sodium | 75 | 5 | 75 | 5 | 53.6 | 3.57 | 0 | 0 |
| Stearic Acid | 7.5 | 0.5 | 7.5 | 0.5 | 10.6 | 0.71 | 0 | 0 |
| EXTRAGRANULAR | | | | | | | | |
| Microcrystalline Cellulose | 0 | 0 | 0 | 0 | 402.9 | 26.86 | 322.3 | 26.86 |
| Croscarmellose Sodium | 0 | 0 | 0 | 0 | 21.4 | 1.43 | 17.2 | 1.43 |
| Stearic Acid | 7.5 | 0.5 | 7.5 | 0.5 | 4.3 | 0.29 | 3.5 | 0.29 |
| Total | 1500 | 100 | 1500 | 100 | 1500 | 100 | 1200 | 100 |

*NAC1B70%01 = 70% NACA + 12% Lactose + 12MCC + 5% Croscarmellose Sodium + 1% Stearic Acid NACA Tablet Dry Blend Formulation Development NACA Tablet formulations (Table 15) were dry blended and directly compressed. The flow of formulation from the hopper to the press was not uniform. Also, the resulting tablets suffered poor friability, hardness and capping. As a result dry blending was abandoned.

TABLE 15

Composition of Prototype NACA Tablet Dry Blend Formulations

| | Prototype Batch Composition | | | |
|---|---|---|---|---|
| | Batch NAC1B50%0101 | | Batch NAC1B50%201 | |
| Component | g | % | g | % |
| NACA | 600 | 50 | 600 | 50 |
| Lactose | 528 | 44 | — | — |
| Microcrystalline Cellulose | — | — | 528 | 44 |
| Croscarmellose Sodium | 60 | 5 | 60 | 5 |
| Stearic Acid | 12 | 1 | 12 | 1 |
| Total | 1200 | 100 | 1200 | 100 |

The formulations described above can also be used as a dry blend for filling into capsules.

The relation between micronization conditions and an initial increase of the degradation product diNACA was further investigated. Comparing stainless steel and zirconium oxide grinding jars gives a clear indication that steel samples undergo a time dependent increase of the degradation product diNACA. In contrast, using zirconium oxide jars and balls did not lead to an initial increase of the degradation product diNACA. Therefore the zirconium oxide milling process was further investigated and successfully optimized regarding particle size distribution, milling parameters and impurity profile for the 1% NACA formulation. Zirconium oxide milling process was investigated and successfully optimized regarding particle size distribution, milling parameters and impurity profile for the 1% NACA formulation. The particle size distribution by laser diffraction analysis was $x_{10}$=1.3 µm, $x_{50}$=4.7 µm and $x_{90}$=12.3 µm. Batches were prepared and found to be stable for up to 4 weeks at ambient temperature.

Single Crystal X-ray Diffraction.

The absolute structure of NACA has been determined by single crystal X-ray diffraction from suitable crystals grown from cooling of a saturated 2-propanol NACA solution to ambient conditions. Single crystal analysis of crystals clearly shows that the material is NACA with the expected bond connectivity. The absolute stereochemistry has been proved in the crystal with excellent confidence, as confirmed by the Flack parameter being −0.02(3). The density of the material is high, reducing the risk that a more stable polymorph is even possible and the hydrogen bonding network observed satisfies the expected functionality observed in NACA. The predicted XRPD from the SC-XRD data is consistent with the Form 1 material, indicating that the crystal was representative of the bulk material. Data was collected and found to be twinned, therefore, was refined accordingly using HKLF5 and BASF commands, locating a two component twin with BASF scales 0.7271(10):0.2729(10) in the Monoclinic space group P21 where two complete formula units of NACA were found in the asymmetric unit only. No disorder was noted in the final structure with final a R1 [I>2σ(I)] of 3.30% obtained with Flack parameter of −0.02 with e.s.d 0.03 determined using 1549 quotients that is suitable to accurately determine the IUPAC name of NACA as 2R)-2-(acetylamino)-3-sulfanylpropanamide (=N-acetyl-L-cysteine amide=(R)-2-acetylamino)-3-mercapto-propamide).

NACA, Form 1 overall structure quality factor: 1

Where:

1. Strong data set, no disorder, R1~4%. Publishable quality.

2. Good data set, contains some minor disorder, R1~6%. Publishable quality.

3. Average data set and/or easily modelled disorder or twinning. Publishable with care.

4. Weak data and/or major disorder or twinning that is not easily modelled. Publishable in some cases.

5. Very weak data and/or unexplained features of data or model. Not of publishable quality.

Polymorphism.

A detailed polymorph screen of NACA (NACA) (NACA) has been performed using a variety of solvents and experimental conditions. During the primary screen, the most common solid form observed was pattern 1 (Table 16).

TABLE 16

Crystallographic parameters and refinement indicators of NACA, Form 1. NACA, Form 1

| | |
|---|---|
| Empirical formula | $C_5H_{10}N_2O_2S$ |
| Formula weight | 162.21 |
| Temperature/K | 120(1) |
| Crystal system | Monoclinic |
| Space group | $P2_1$ |
| a/Å | 7.2832(2) |
| b/Å | 7.5542(2) |
| c/Å | 13.9686(4) |
| α/° | 90 |
| β/° | 98.6983(15) |
| γ/° | 90 |
| Volume/Å$^3$ | 759.70(4) |
| Z, Z' | 4.2 |
| $\rho_{calc}$ g/cm$^3$ | 1.418 |
| μ/mm$^{-1}$ | 0.369 |
| F(000) | 344.0 |
| Crystal size/mm$^3$ | 0.384 × 0.207 × 0.131 |
| Radiation | MoKα (λ = 0.71073) |
| 2Θ range for data collection/° | 2.95 to 56.582 |
| Index ranges | −9 ≤ h ≤ 9, −10 ≤ k ≤ 10, −18 ≤ l ≤ 18 |
| Reflections collected | 5810 |
| Independent reflections | 5810 [$R_{int}$ = 0.0580, $R_{sigma}$ = 0.0288] |
| Data/restraints/parameters | 5810/1/186 |
| Goodness of Fit | 1.057 |
| Final R indexes [I > 2σ (I)] | $R_1$ = 0.0330, w$R_2$ = 0.0869 |
| Final R indexes [all data] | $R_1$ = 0.0350, w$R_2$ = 0.0900 |
| Δρmax, Δρmin/e Å$^{-3}$ | 0.47/−0.53 |
| Flack Parameter | −0.02(3) |

$R_1 = (\Sigma |F_o| - |F_c|)/\Sigma |F_o|)$; w$R_2 = \{\Sigma [w(F_o^2 - F_c^2)^2]/\Sigma [w(F_o^2)^2]\}^{1/2}$; $S = \{\Sigma [w(F_o^2 - F_c^2)^2]/(n - p)\}^{1/2}$.

Several experiments yielded diffractogram patterns that were different or, more commonly, had extra peaks observed. The extra peaks would indicate the presence of another form, albeit not in a pure phase.

Attempts to reproduce these forms failed using both crash cooling, evaporation and anti-solvent addition. Analysis of these attempts by NMR showed that the material was still predominately the NACA material and that it had not oxidized to diNACA. The lack of reproducibility of these potential forms is good evidence for their lack of stability. This study has clearly demonstrated that the NACA material exists as Form 1 and that other forms are difficult, if not impossible, to produce.

Approximately 80 mg of NACA was weighed into each of 24 vials. The solvents listed below were added to the appropriate vials. The quantities added were calculated (based on solubility studies) to dissolve approx. 60% of the material. These mixtures were temperature cycled between ambient and 40° C., in 4 hr cycles, for 72 hrs. Solids isolated from the slurries are tested by)(RFD. The resulting saturated solutions were separated into three separated vials for crash cooling, anti-solvent addition and evaporation experiments.

TABLE 17

List of Solvents Used in the Primary Polymorph Screen

| | Solvent |
|---|---|
| 1 | Acetone |
| 2 | Acetone/water (80:20) |
| 3 | Acetone/Heptane (75:25) |
| 4 | Acetonitrile |
| 5 | Acetonitrile/water (80:20) |
| 6 | 1-Butanol |
| 7 | 1,2-Dimethoxyethane |
| 8 | 1,4-Dioxane |
| 9 | Dioxane/water (80:20) |
| 10 | Ethanol |
| 11 | Ethanol/water (80:20) |
| 12 | Ethanol/heptane (75:25) |
| 13 | Ethyl Formate |
| 14 | Isopropyl acetate |
| 15 | Ethyl acetate |
| 16 | Methanol |
| 17 | Methanol/water (80:20) |
| 18 | Methyl Ethyl ketone |
| 19 | Nitromethane |
| 20 | 1-Propanol |
| 21 | 2-Propanol |
| 22 | 2-Propanol/water (80:20) |
| 23 | Tetrahydrofuran |
| 24 | Water |

Liquid Chromatography with Mass Spectrometric Detection
Column Temperature: 30° C.
Mobile Phase A: 0.1% v/v Formic in Water
Mobile Phase B: 0.1% v/v Formic in Acetonitrile
Diluent: Mobile Phase A: 50:50 Water:Acetonitrile
Flow Rate: 1.0 mL/min
Runtime: 25 minutes
Injection Volume: 10 μL
Detection: 190-400 nm Gradient:

| Time (minutes) | Solvent B [%] |
|---|---|
| 0 | 0 |
| 12 | 10 |
| 15 | 100 |
| 15.1 | 100 |
| 25 | 0 |

Instrument: LCQ Advantage Ion Trap MS
Sample concentration: 1 mg/ml, +ve ion mode by infusion
Source voltage (kV): 4.50
Source current (µA): 80.00
Sheath gas flow rate: 20.00
Aux/Sweep gas flow rate: 0.00
Capillary voltage (V): 8.00
Capillary temp (° C.): 200
Tube lens (V, Sp): 40.00

Figure 15:
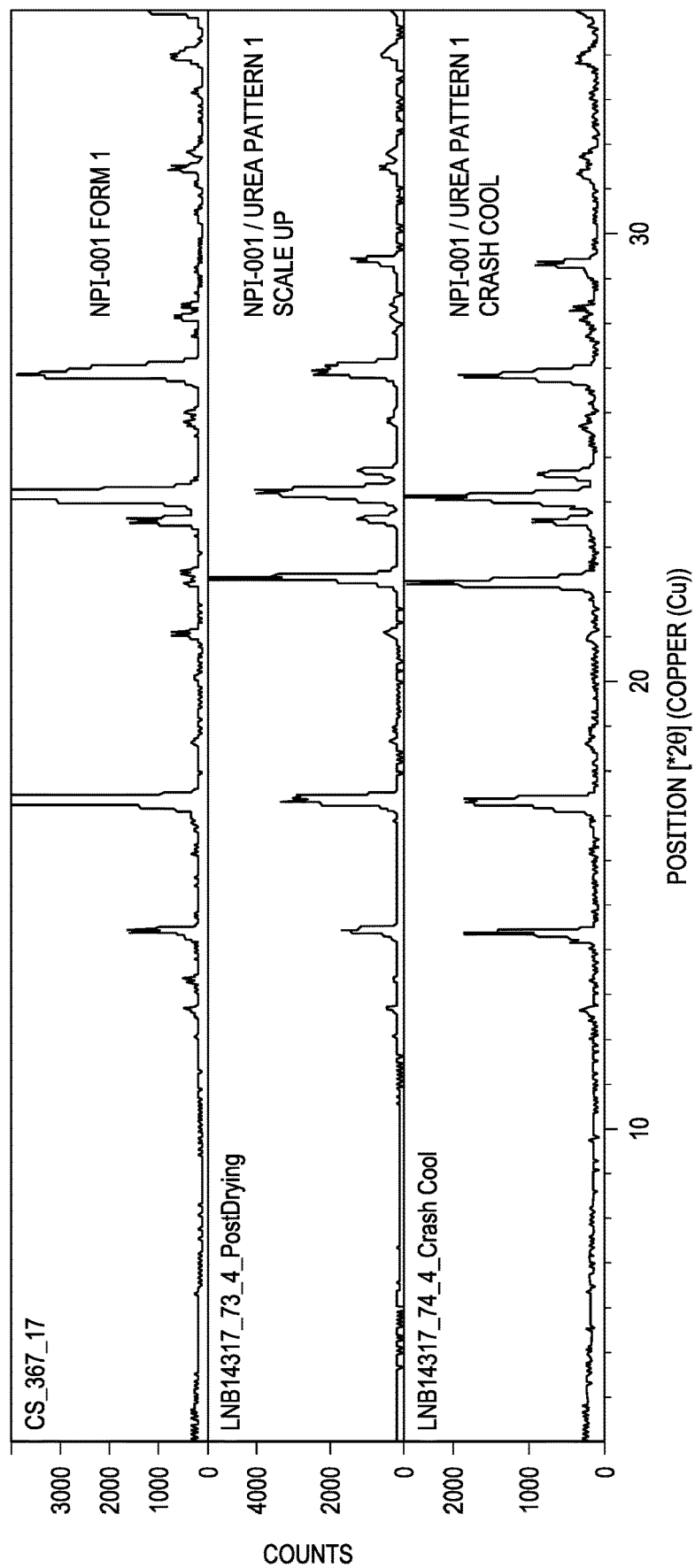
FIG. 15 shows XRPD of NPI-001 Form 1, NPI-001/urea pattern 1 and NPI-001/urea pattern 1 Crash Cool.

NACA/Urea Co-crystal. A primary co-crystal screen was conducted where 28 potential co-crystal formers (CCFs) were screened (Table 18) in 6 solvent systems under 2 process relevant crystallization conditions, namely, thermal maturation and evaporation. A NACA/urea co-crystal was identified (FIG. 15). The NACA/urea pattern 1 material was successfully scaled up from four solvents as a part of the secondary co-crystal screen, then fully characterized where it was found to be crystalline by XPRD and PLM with the expected XRPD pattern, thermally stable with high purity. NMR analysis confirmed an approximate stoichiometric content of urea contained within the material. The material appeared to be stable under ambient conditions and elevated temperature (80° C.) but unstable when stored at high humidity for prolonged periods, showing degradation to the diNACA. No signs of dissociation were identified in organic solvents and solvent/water mixtures with low water activity but was found to dissociate in deionized water and solvent/water mixtures with a high water activity. An additional DSC experiment with post-XRPD analysis confirmed that the exothermic event observed during the DSC cooling cycle is a recrystallization to NACA.

TABLE 18

Primary Co-Crystal Screen Co-Former List

|  | Co-Former | GRAS* |
|---|---|---|
| 1 | 2-Picolinamide | Yes |
| 2 | 5-Methylfurfural | Yes |
| 3 | 5-Methylfurfurylamine | Yes |
| 4 | Adenine | Yes |
| 5 | Citric Acid | Yes |
| 6 | Glycine | Yes |
| 7 | Hippuric Acid | Yes |
| 8 | L-Aspartic Acid | Yes |
| 9 | L-Proline | Yes |
| 10 | L-Tyrosine | Yes |
| 11 | Malonic Acid | Yes |
| 12 | Melamine | Yes |
| 13 | Oxalic Acid | Yes |
| 14 | Theophylline | Yes |
| 15 | Tromethamine | Yes |
| 16 | Urea | Yes |
| 17 | Xanthine | Yes |
| 18 | 3,4-Dihydroxybenzoic Acid | Yes |
| 19 | Camphoric Acid | Yes |
| 20 | Cytosine | Yes |
| 21 | Formamide | Yes |
| 22 | L-Cysteine | Yes |
| 23 | L-Methionine | Yes |
| 24 | L-Serine | Yes |
| 25 | Threonine | Yes |
| 26 | DiNACA | Yes |
| 27 | N-Acetyl-L-cysteine | Yes |
| 28 | Succinic acid | Yes |

*GRAS: generally recognized as safe

Figure 16:
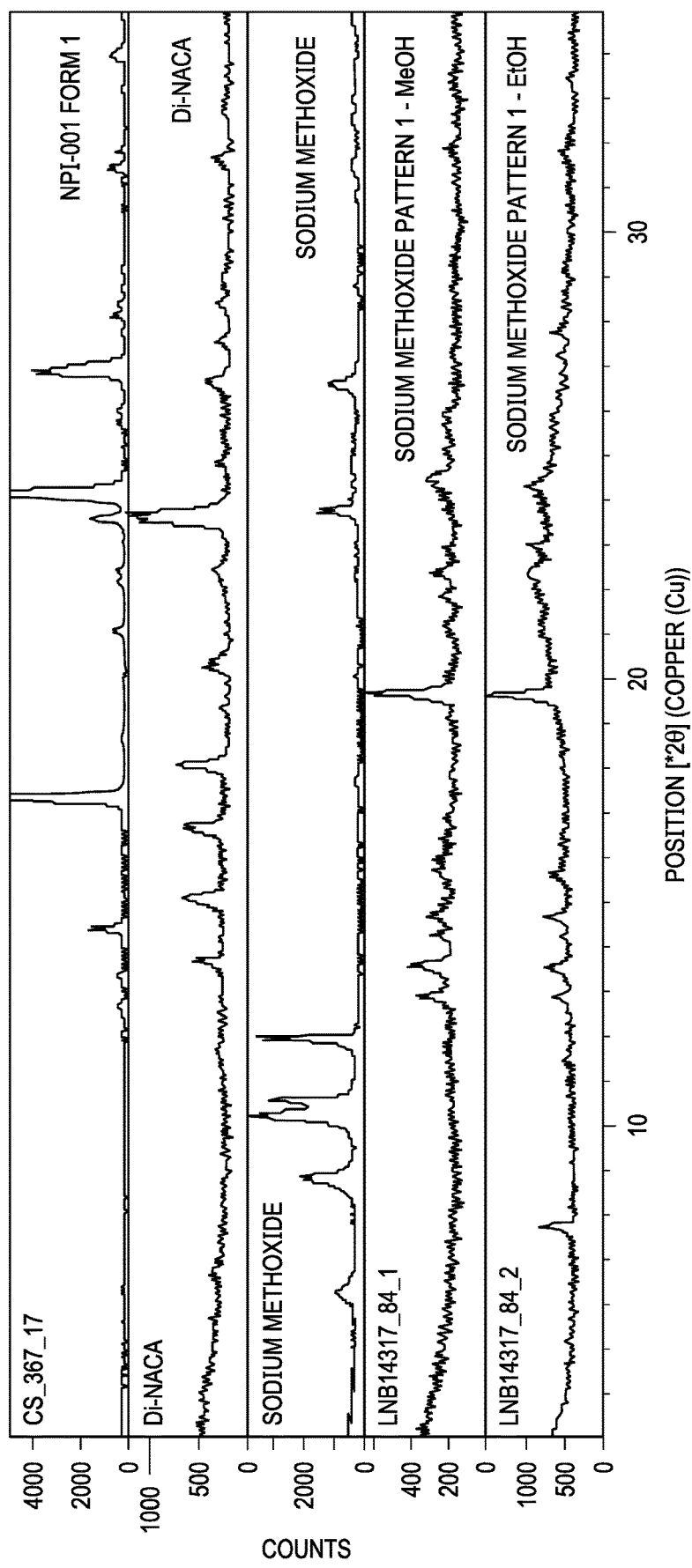
FIG. 16 shows XRPD Diffractograms of NPI-001 Form 1, diNACA, Sodium Methoxide, NPI-001/sodium methoxide pattern 1 from methanol and NPI-001/sodium methoxide pattern 1 from ethanol.

NACA Sodium Salt. A salt screen was conducted using 6 solvent systems under 2 process-relevant crystallization conditions, namely thermal maturation and evaporation. From this study, one sodium salt was identified. The salt was formed using sodium methoxide from either acetonitrile, ethanol, methanol, or tetrahydrofuran as shown in FIG. 16.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A process for making N-acetylcysteine amide (NACA) comprising:
    contacting cystine with methanol and a chlorinating reagent to form an organic solution containing cystine dimethylester dihydrochloride and optionally isolating and drying the cystine dimethylester dihydrochloride;
    combining a dried or undried cystine dimethylester dihydrochloride with triethylamine, acetic anhydride, and acetonitrile to form a di-N-acetylcystine dimethylester and optionally isolating and drying the di-N-acetylcystine dimethylester;
    mixing a dried or undried di-N-acetylcystine dimethylester with ammonium hydroxide to form a di-N-acetylcystine amide and optionally isolating and drying the di-N-acetylcystine amide; and
    reducing a dried or undried di-N-acetylcystine amide to a N-acetylcysteine amide with a reducing agent, triethylamine and an organic solvent or alcohol.

2. The process of claim 1, wherein the alcohol is an organic alcohol selected from an alkyl alcohol, methanol, ethanol, propanol, isopropanol or butanol.

3. The process of claim 1, wherein the cystine is contacted with the methanol and the chlorinating agent at −10 to 10° C. and then the mixture is heated to reflux at 65 to 70° C. until completion to form the organic solution containing the cystine dimethylester dihydrochloride.

4. The process of claim 1, wherein the chlorinating reagent is thionyl chloride.

5. The process of claim 1, further comprising a solvent exchange between the contacting and the combining steps.

6. The process of claim 1, wherein the step of combining is performed at −10 to 10° C.

7. The process of claim 1, wherein a precipitate is formed in the combining step and the precipitate is filtered and washed with ethyl acetate before drying under vacuum.

8. The process of claim 1, wherein the step of combining uses acetonitrile at −10 to 10° C. before adding triethylamine followed by acetic anhydride.

9. The process of claim 1, further comprising drying the di-N-acetylcystine amide with a drying agent before the di-N-acetylcystine amide is reduced.

10. The process of claim 1, wherein triethylamine hydrochloride is also produced as a product of the combining step, and the process further comprises treating the triethylamine hydrochloride with a saturated sodium bicarbonate solution to produce free based triethylamine.

11. The process of claim 1, wherein the ammonium hydroxide is in an aqueous solution.

12. The process of claim 1, wherein the di-N-acetylcystine dimethylester is dried and wherein the mixing of the dried di-N-acetylcystine dimethylester with ammonium hydroxide is performed at room temperature.

13. The process of claim 1, wherein no metals are used in the reduction of di-N-acetylcystine amide into N-acetylcysteine amide.

14. The process of claim 1, wherein the process is carried out in the absence of trace metal ion impurities which could catalyze oxidation of the NACA.

15. The process of claim 1, further comprising removing the methanol under reduced pressure at about 45° C. or less before the cystine dimethylester dihydrochloride is used in the combining step.

16. The process of claim 1, further comprising removing the methanol under reduced pressure at about 35° C. or less before the cystine dimethylester dihydrochloride is used in the combining step.

17. The process of claim 1, further comprising removing the methanol under reduced pressure at about 30° C. or less before the cystine dimethylester dihydrochloride is used in the combining step.

18. The process of claim 1, further comprising removing the methanol under reduced pressure at about 45° C. before the cystine dimethylester dihydrochloride is used in the combining step.

19. The process of claim 1, wherein the product mixture from the combining step is filtered to remove solids.

20. The process of claim 1, wherein the reducing agents is one or more selected from tris (2-carboxyethyl)phosphine, thioglycolic acid, and dithiothreitol, and the organic solvent is THF, dichloromethane (DCM), isopropanol, or ethanol.

21. The process of claim 1, wherein the NACA is prepared batchwise under Good manufacturing Practices (GMP) conditions to produce a batch size greater than 1 kg.

22. The process of claim 1, wherein the NACA is prepared batchwise under GMP conditions to produce a batch size greater than 15 kg.

23. The process of claim 1, wherein the NACA is prepared batchwise under GMP conditions to produce a batch size greater than 50 kg.

24. The process of claim 1, wherein the NACA is prepared batchwise under GMP conditions to produce a batch size greater than 100 kg.

25. The process of claim 1, further comprising masking the sulfurous odor and taste of NACA by solubilization in a flavoring and sweetening agent water solution.

26. The process of claim 1, further comprising suspending the NACA in perfluorohexyloctane.

27. The process of claim 1, further comprising solubilizing the NACA in a phosphate buffer.

28. A process for making N-acetylcysteine amide comprising:
   contacting cystine with methanol and a chlorinating reagent to form an organic solution containing a cystine dimethylester dihydrochloride and optionally isolating and drying the cystine dimethylester dihydrochloride;
   combining a dried cystine dimethylester dihydrochloride with triethylamine, acetic anhydride, and acetonitrile to form a di-N-acetylcystine dimethylester and optionally isolating and drying the di-N-acetylcystine dimethylester;
   mixing a dried di-N-acetylcystine dimethylester with ammonium hydroxide to form a di-N-acetylcystine amide and optionally isolating and drying the di-N-acetylcystine amide; and
   reducing a dried di-N-acetylcystine amide to a N-acetylcysteine amide with dithiothreitol, triethylamine, and an alcohol, wherein the reduction is without the presence of a metal.

29. A process for making (2R,2R')-3,3'-disulfanediyl bis (2-acetamidopropanamide) (DiNACA) comprising:
   contacting cystine with methanol and a chlorinating reagent to form an organic solution containing a cystine dimethylester dihydrochloride and optionally isolating and drying the cystine dimethylester dihydrochloride;
   combining a dried or undried cystine dimethylester dihydrochloride with triethylamine, acetic anhydride, and acetonitrile to form a di-N-acetylcystine dimethylester and isolating and drying the di-N-acetylcystine dimethylester; and
   mixing a dried di-N-acetylcystine dimethylester with ammonium hydroxide to form the (2R,2R')-3,3'-disulfanediyl bis(2-acetamidopropanamide) and optionally isolating and drying the (2R,2R')-3,3'-disulfanediyl bis (2-acetamidopropanamide).

* * * * *